United States Patent

Rane

(10) Patent No.: US 7,585,864 B2
(45) Date of Patent: Sep. 8, 2009

(54) FARNESYL PROTEIN TRANSFERASE INHIBITORS AND THEIR USE TO TREAT CANCER

(75) Inventor: Dinanath F. Rane, Morganville, NJ (US)

(73) Assignee: Schering Corporation, Kenilworth, NJ (US)

(*) Notice: Subject to any disclaimer, the term of this patent is extended or adjusted under 35 U.S.C. 154(b) by 309 days.

(21) Appl. No.: 11/301,308

(22) Filed: Dec. 12, 2005

(65) Prior Publication Data

US 2006/0154937 A1   Jul. 13, 2006

Related U.S. Application Data

(60) Provisional application No. 60/635,708, filed on Dec. 13, 2004.

(51) Int. Cl.
*A61K 31/497* (2006.01)
*C07D 241/04* (2006.01)
*C07D 295/00* (2006.01)

(52) U.S. Cl. .................. 514/252.12; 544/358

(58) Field of Classification Search ............... None
See application file for complete search history.

(56) References Cited

U.S. PATENT DOCUMENTS

| | | | |
|---|---|---|---|
| 5,672,611 A | 9/1997 | Doll et al. | |
| 5,712,280 A | 1/1998 | Doll et al. | |
| 6,130,229 A * | 10/2000 | Afonso et al. | 514/291 |
| 6,362,188 B1 | 3/2002 | Guzi et al. | |
| 2006/0211706 A1 | 9/2006 | Mallams | |
| 2007/0213340 A1 | 9/2007 | Kelly et al. | |

FOREIGN PATENT DOCUMENTS

| | | |
|---|---|---|
| WO | WO 96/31478 A1 | 10/1996 |
| WO | WO 98/57960 A1 | 12/1998 |
| WO | WO 00/37459 A1 | 6/2000 |
| WO | WO 02/056884 A2 | 7/2002 |
| WO | WO 02/080895 A2 | 10/2002 |
| WO | WO2006065828 * | 6/2006 |

OTHER PUBLICATIONS

"Cancer definition", http://www.medterms.com/script/main/art.asp?articlekey=2580, accessed Nov. 27, 2007.*
Palmer et al., Expert Opinion in Investigational Drugs, 2004, 13(12), 1555-68.*
Saba et al., Expert Opinion in Investigational Drugs, 2004, 13(6), 609-29*
Banerji et al., Expert Opinion in Therapeutic Targets, 2004, 8(3), 221-39.*
Fahn et al., Expert Opinion in Emerging Drugs, 2004, 9(2), 313-34.*
Rhee et al., Expert Opinion in Emerging Drugs, 2004, 9(1), 91-104.*
PCT International Search Report dated May 29, 2006 for corresponding PCT Application No. PCT/US2005/045098.
Schering-Plough Discontinues Phase III Clinical Study of Sarasar(TM) (Lonafarnib) in Non-Small-Cell Lung Cancer, Schering-Plough Press Release, Feb. 5, 2004.

* cited by examiner

*Primary Examiner*—James O Wilson
*Assistant Examiner*—Noble Jarrell
(74) *Attorney, Agent, or Firm*—Henry C. Jeanette

(57) ABSTRACT

Disclosed are compounds of the formula:

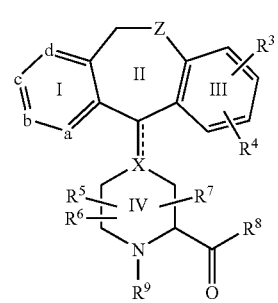

(1.0)

wherein $R^8$ represents a cyclic and acyclic moiety to which is bound an imidazolylalkyl group; $R^9$ represents a carbamate, urea, amide or sulfonamide group; and the remaining substituents are as defined herein. Also disclosed is a method of treating cancer and a method of inhibiting farnesyl protein transferase using the disclosed compounds.

14 Claims, No Drawings

FARNESYL PROTEIN TRANSFERASE INHIBITORS AND THEIR USE TO TREAT CANCER

REFERENCE TO RELATED CASES

This application claims the benefit of U.S. Provisional Application Ser. No. 60/635708 filed on Dec. 13, 2004.

BACKGROUND

WO 95/10516 (published Apr. 20, 1995), WO96/31478 (published Oct. 10, 1996), U.S. Pat. No. 5,801,175 (issued Sep. 1, 1998), U.S. Pat. No. 6,214,827 (issued Apr. 10, 2001), WO 98/57960 (published Dec. 23, 1998), WO 00/37458 (published Jun. 29, 2000), U.S. Pat. No. 6,362,188 (issued Mar. 26, 2002), WO 00/37459 (published Jun. 29, 2000), U.S. Pat. No. 6,372,747 (issued Apr. 16, 2002), and U.S. Pat. No. 6,740,661 (issued May 25, 2004) disclose compounds useful for inhibiting farnesyl protein transferase.

In view of the current interest in farnesyl protein transferase inhibitors and their use for treating cancer, novel farnesyl protein transferase inhibitors would be a welcome contribution to the art. This invention provides such a contribution.

SUMMARY OF THE INVENTION

In its many embodiments, the invention provides a novel class of farnesyl protein transferase (FPT) inhibitors, methods of preparing such compounds, pharmaceutical compositions comprising one or more such compounds, methods of preparing pharmaceutical formulations comprising one or more such compounds and methods of treatment, prevention, inhibition or amelioration of one or more proliferative diseases such as cancer.

Thus, this invention provides compounds (FPT Inhibitors) of formula 1.0:

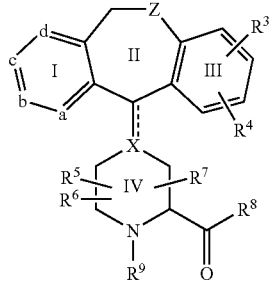

(1.0)

or the pharmaceutically acceptable salts thereof, wherein:

one of a, b, c and d represents N or $N^+O^-$, and the remaining a, b, c and d groups represent $CR^1$ or $CR^2$; or each of a, b, c, and d are independently selected from the group consisting of: $CR^1$ and $CR^2$;

each $R^1$ and each $R^2$ is independently selected from the group consisting of: H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —$N(R^{10})_2$, —$NO_2$, —$OC(O)R^{10}$, —$CO_2R^{10}$, —$OCO_2R^{11}$, —CN, —$NR^{10}COOR^{11}$, —$SR^{11}C(O)OR^{11}$ (e.g., —$SCH_2CO_2CH_3$), —$SR^{11}N(R^{75})_2$ (provided that $R^{11}$ in —$SR^{11}N(R^{75})_2$ is not —$CH_2$—) wherein each $R^{75}$ is independently selected from H or —$C(O)OR^{11}$ (e.g., —$S(CH_2)_2NHC(O)O$-t-butyl and —$S(CH_2)_2NH_2$), benzotriazol-1-yloxy, tetrazol-5-ylthio, substituted tetrazol-5-ylthio (e.g., alkyl substituted tetrazol-5-ylthio such as 1-methyl-tetrazol-5-ylthio), alkynyl, alkenyl and alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$-$C_7$ fused ring to the benzene ring (Ring III);

$R^5$, $R^6$, and $R^7$ each independently represents H, —$CF_3$, —$COR^{10}$, alkyl or aryl, said alkyl or aryl optionally being substituted with one or more substitutents selected from the group consisting of: —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, and —$OPO_3R^{10}$, or $R^5$ is combined with $R^6$ to represent =O or =S; provided that for the groups —$OR^{10}$, —$SR^{10}$, and —$N(R^{10})_2$ $R^{10}$ is not H;

$R^{10}$ represents H, alkyl, aryl, or aralkyl (e.g., benzyl);

$R^{11}$ represents alkyl or aryl;

X represents N, CH or C, and when X is C the optional bond (represented by the dotted line) to carbon atom 11 is present, and when X is CH the optional bond (represented by the dotted line) to carbon atom 11 is absent;

Z is selected from the group consisting of: —O—, —S—, —S(O)—, —$S(O_2)$—, and —$N(R^{10})$—;

$R^8$ represents a heterocyclic ring selected from the group consisting of:

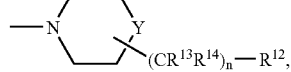
(2.0)

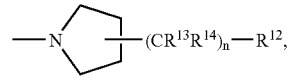
(3.0)

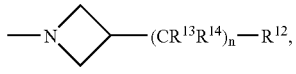
(4.0)

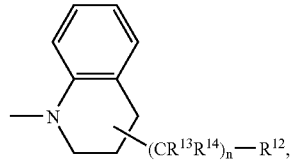
(5.0)

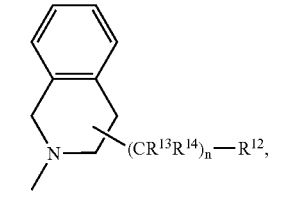
(6.0)

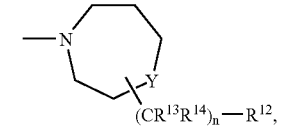
(7.0)

-continued

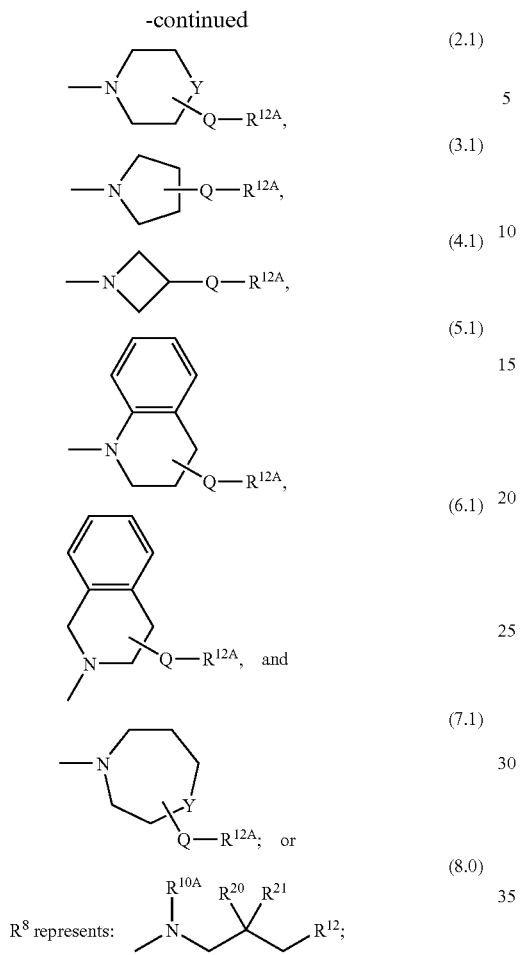

said $R^8$ heterocyclic rings (2.0 to 7.0 and 2.1 to 7.1) being optionally substituted with one or more substituents independently selected from the group consisting of:
  (a) alkyl (e.g., methyl, ethyl, isopropyl, and the like);
  (b) substituted alkyl wherein said substituents are selected from the group consisting of: halo, aryl, —$OR^{15}$, —$N(R^{15})_2$, heteroaryl, heterocycloalkyl, and cycloalkyl, wherein each $R^{15}$ group is the same or different, provided that said optional substituent is not bound to a carbon atom that is adjacent to an oxygen or nitrogen atom, and wherein $R^{15}$ is selected from the group consisting of: H, alkyl, aryl, arylalkyl, heteroaryl, heteroarylalkyl, cycloalkyl, and cycloalkylalkyl;
  (c) hydroxyl, with the proviso that carbon atoms adjacent to the nitrogen, sulfur or oxygen atoms of the ring are not substituted with hydroxyl;
  (d) alkyloxy; and
  (e) arylalkyloxy;

(i.e., each substitutable H atom on each substitutable carbon atom in said heterocyclic rings is optionally replaced with substituents selected from (a) to (e) as defined above);

Y represents —$CH_2$—, —$NR^{16}$—, —O—, —S—, —S(O)—, or —$S(O_2)$— wherein $R^{16}$ is selected from the group consisting of: H, alkyl, cycloalkyl, cycloalkylalkyl, aryl, arylalkyl, heteroaryl, heteroarylalkyl, acyl, aroyl, carbamoyl, carboxamido, alkylsulfonyl, arylsulfonyl, arylalkylsulfonyl, sulfonamido, alkylsulfonamido, arylsulfonamido and arylalkylsulfonamido;

n is 0 to 6 (preferably 1-3);
Q represents —O— or —N—, provided that Q is not adjacent to a heteroatom in the heterocycloalkyl rings of 2.1, 3.1, 4.1, 5.1, 6.1 and 7.1;

$R^{10A}$ is selected from the group consisting of: H, $C_3$ to $C_4$ alkyl (preferably branched chain alkyl, and most preferably $C_4$ to $C_7$ branched chain alkyl), aryl, arylalkyl, heteroaryl, heteroarylalkyl, cycloalkyl, cycloalkylalkyl, substituted alkyl, substituted aryl, substituted arylalkyl, substituted heteroaryl, substituted heteroarylalkyl, substituted cycloalkyl, and substituted cycloalkylalkyl;

$R^{12}$ is selected from the group consisting of:

(e.g., $R^{12}$ is 10.0);
  wherein $R^{17}$ is selected from the group consisting of: (1) H, (2) alkyl, (3) aryl, (4) arylalkyl, (5) substituted arylalkyl wherein the substituents are selected from the group consisting of: halo (e.g., F and Cl) and CN, (6) —C(aryl)$_3$ (e.g., —C(phenyl)$_3$, i.e., trityl), (7) cycloalkyl, (8) substituted alkyl (as defined above in (b)), and (9) cycloalkylalkyl;

$R^{12A}$ is selected from the group consisting of: rings 9.0, 9.1 and 11.0, as defined above;

said imidazolyl ring 9.0 and 9.1 optionally being substituted with one or two substituents, said imidazole ring 10.0 optionally being substituted with 1-3 substituents, and said pyridyl ring 9.1 optionally being substituted with 1-4 substituents, wherein said optional substituents for rings 9.0, 9.1, 10.0 and 11.0 are bound to the carbon atoms of said rings and are independently selected from the group consisting of: —NHC(O)$R^{15}$, —$C(R^{18})_2 OR^{19}$, —$OR^{15}$, —$SR^{15}$, F, Cl, Br, alkyl (e.g., methyl, such as 4-methyl in 10.0), substituted alkyl (as defined above in (b)), aryl, arylalkyl, cycloalkyl, or —$N(R^{15})_2$; $R^{15}$ is as defined above; each $R^{18}$ is independently selected from the group consisting of: H and alkyl (preferably —$CH_3$), preferably H; $R^{19}$ is selected from the group consisting of: H and —C(O)$NHR^{20}$, and $R^{20}$ is as defined below;

$R^{13}$ and $R^{14}$ for each n are independently selected from the group consisting of: H, F, alkyl, aryl, arylalkyl, heteroaryl, heteroarylalkyl, cycloalkyl, cycloalkylalkyl, —CON($R^{15})_2$ (wherein $R^{15}$ is as defined above), —$OR^{15}$ and —$N(R^{15})_2$ provided that the —$OR^{15}$ and —$N(R^{15})_2$ groups are not bound to a carbon atom that is adjacent to a nitrogen atom, and provided that there can be only one —OH group on each carbon; and the substitutable $R^{13}$ and $R^{14}$ groups are optionally substituted with one or more (e.g., 1-3) substituents selected from the group consisting of: F, alkyl (e.g., methyl, ethyl, isopropyl, and the like), cycloalkyl, arylalkyl, and heteroarylalkyl (i.e., the $R^{13}$ and/or $R^{14}$ groups can be unsubtituted or can be substituted with 1-3 of the substituents described above, except when $R^{13}$ and/or $R^{14}$ is H); or $R^{13}$ and $R^{14}$, for each n, together with the carbon atom to which they are bound, form a $C_3$ to $C_6$ cycloalkyl ring;

$R^9$ is selected from:

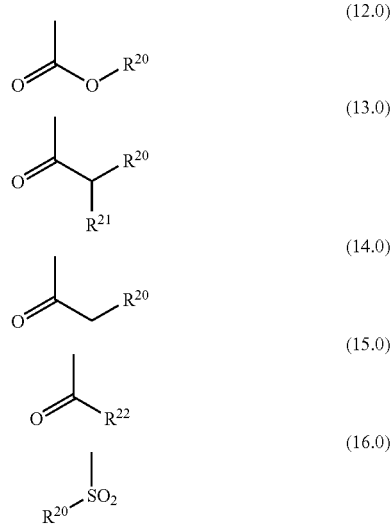

$R^{20}$ is selected from the group consisting of: H, alkyl, aryl, arylalkyl, cycloalkyl, cycloalkylalkyl, heteroaryl, heteroarylalkyl, heterocycloalkyl, and heterocyloalkylalkyl, provided that $R^{20}$ is not H when $R^9$ is group 12.0 or 16.0;

when $R^{20}$ is other than H, then said $R^{20}$ group is optionally substituted with one or more (e.g., 1-3) substituents selected from the group consisting of: halo, alkyl, aryl, —OC(O)$R^{15}$ (e.g., —OC(O)CH$_3$), —OR$^{15}$ and —N(R$^{15}$)$_2$, wherein each $R^{15}$ group is the same or different, and wherein $R^{15}$ is as defined above, provided that said optional substituent is not bound to a carbon atom that is adjacent to an oxygen or nitrogen atom;

$R^{21}$ is selected from the group consisting of: H, alkyl, aryl, arylalkyl, cycloalkyl, cycloalkylalkyl, heteroaryl, heteroarylalkyl, heterocycloalkyl and heterocycloalkylalkyl; and when $R^{21}$ is other than H, then said $R^{21}$ group is optionally substituted with one or more (e.g., 1-3) substituents selected from the group consisting of: alkyl and aryl; and $R^{22}$ is selected from the group consisting of: cycloalkyl (e.g., cyclopropylmethyl, i.e.,

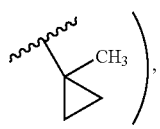

heterocycloalkyl, aryl (e.g., phenyl), substituted aryl (e.g., halo as a substituent, such as F or Cl), alkyl (e.g., t-butyl), substituted alkyl (substituents include —OH, —CO$_2$H, and —C(O)NH$_2$) and substituted cycloalkyl (substituents include —OH, —CO$_2$H, and —C(O)NH$_2$).

Thus, in one embodiment of this invention $R^9$ is 12.0. In another embodiment $R^9$ is 13.0. In another embodiment $R^9$ is 14.0. In another embodiment $R^9$ is 15.0. In another embodiment $R^9$ is 16.0.

This invention also provides a pharmaceutical composition comprising an effective amount of at least one compound of formula 1.0 and a pharmaceutically acceptable carrier.

This invention also provides a pharmaceutical composition comprising an effective amount of a compound of claim 1 and a pharmaceutically acceptable carrier.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount of the tricyclic compounds described above. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of a compound of this invention to a mammal (e.g., a human) in need of such treatment. In particular, this invention provides a method for inhibiting or treating the growth of tumors expressing an activated Ras oncogene by the administration of an effective amount of a compound of this invention. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, melanoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The compounds of this invention useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

MH+—represents the molecular ion plus hydrogen of the molecule in the mass spectrum;

BOC—represents tert-butyloxycarbonyl;

BOC-ON—represents 1-(tert-butoxycarbonyl)-2-tert-butyl-3-methyl-4-imidazolidinone nitrile;

CBZ—represents —C(O)OCH$_2$C$_6$H$_5$ (i.e., benzyloxycarbonyl);

CBZ-OSUC—represents benzyloxycarbonyl-O-succinimide;

CH$_2$Cl$_2$—represents dichloromethane;

CIMS—represents chemical ionization mass spectrum;

DEAD—represents diethylazodicarboxylate;

DEC—represents EDC which represents 1-(3-dimethylaminopropyl)-3-ethylcarbodiimide hydrochloride;

DMF—represents N,N-dimethylformamide;

Et—represents ethyl;

EtOAc—represents ethyl acetate;

EtOH—represents ethanol;

HOBT—represents 1-hydroxybenzotriazole hydrate;

IPA—represents isopropanol;

iPrOH—represents isopropanol;

LAH—represents lithium aluminum hydride;

LDA—represents lithium diisopropylamide;

MCPBA—represents meta-chloroperbenzoic acid;

Me—represents methyl;

MeOH—represents methanol;

MS—represents mass spectroscopy;

NMM—represents N-methylmorpholine;

Ph—represents phenyl;

Pr—represents propyl;

TBDMS—represents tert-butyidimethylsilyl;

TEA—represents triethylamine;

TFA—represents trifluoroacetic acid;

THF—represents tetrahydrofuran;

Tr—represents trityl;

"Anti-cancer agent", "chemotherapeutic agent", and "antineoplastic agent" have the same meaning, and these terms represent the drugs (medicaments) used to treat cancer;

"Antineoplastic agent" represents a chemotherapeutic agent effective against cancer;

"At least one" means one or more than one, e.g., 1, 2 or 3, or 1 or 2, or 1;

"Compound", with reference to the antineoplastic agents, includes the agents that are antibodies;

"Concurrently" represents (1) simultaneously in time (e.g., at the same time); or (2) at different times during the course of a common treatment schedule;

"Consecutively" means one following the other;

"Different", as used in the phrase "different antineoplastic agents", means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound;

"Effective amount" or "therapeutically effective amount" is meant to describe an amount of compound or a composition of the present invention effective in inhibiting or treating the cancer, or effective in inhibiting farnesyl protein transferase; For example, the amount of the compound or composition that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor; Also, for example, a therapeutically effective amount of the FPT inhibitor is that amount which results in the reduction of farnesylation; the reduction in farnesylation may be determined by the analysis of pharmacodynamic markers such as Prelamin A and HDJ-2 (DNAJ-2) using techniques well known in the art;

"Mammal" means humans and other mammalian animals;

"One or more" means at least one, e.g., 1, 2 or 3, 1 or 2, or 1;

"Patient" includes humans and animals (preferably, humans);

"Prodrug" represents compounds that are rapidly transformed, for example, by hydrolysis in blood, in vivo to the parent compound, i.e., to the compounds of formula 1.0 or to a salt and/or to a solvate thereof; A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; The scope of this invention includes Prodrugs of the novel compounds of this invention;

Sequentially means (1) administration of one component of the method ((a) compound of the invention, or (b) chemotherapeutic agent, signal transduction inhibitor and/or radiation therapy) followed by administration of the other component or components; after administration of one component, the next component can be administered substantially immediately after the first component, or the next component can be administered after an effective time period after the first component; the effective time period is the amount of time given for realization of maximum benefit from the administration of the first component; and "Solvate" means a physical association of a compound of this invention with one or more solvent molecules; This physical association involves varying degrees of ionic and covalent bonding, including hydrogen bonding; In certain instances the solvate will be capable of isolation, for example when one or more solvent molecules are incorporated in the crystal lattice of the crystalline solid; "Solvate" encompasses both solution-phase and isolatable solvates; Non-limiting examples of suitable solvates include ethanolates, methanolates, and the like; "Hydrate" is a solvate wherein the solvent molecule is H$_2$O.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as defined below (and as defined below, the alkyl, alkenyl, alkynyl, cycloalkyl, cycloalkenyl and cycloalkynyl moieties can be substituted); The bond to the parent moiety is through the carbonyl; Preferred acyls contain a lower alkyl;

Non-limiting examples of suitable acyl groups include formyl, acetyl, propanoyl, 2-methylpropanoyl, butanoyl and cyclohexanoyl;

"Alkenyl" means an aliphatic hydrocarbon group (chain) comprising at least one carbon to carbon double bond, wherein the chain can be straight or branched, and wherein said group comprises about 2 to about 15 carbon atoms; Preferred alkenyl groups comprise about 2 to about 12 carbon atoms in the chain; and more preferably about 2 to about 6 carbon atoms in the chain; Branched means that one or more lower alkyl groups, such as methyl, ethyl or propyl, are attached to a linear alkenyl chain; "Lower alkenyl" means an alkenyl group comprising about 2 to about 6 carbon atoms in the chain, and the chain can be straight or branched; The term "substituted alkenyl" means that the alkenyl group is substituted by one or more independently selected substituents, and each substituent is independently selected from the group consisting of: halo, alkyl, aryl, cycloalkyl, cyano, alkoxy and —S(alkyl); Non-limiting examples of suitable alkenyl groups include ethenyl, propenyl, n-butenyl, 3-methylbut-2-enyl, n-pentenyl, octenyl and decenyl;

"Alkoxy" means an alkyl-O— group (i.e., the bond to the parent moiety is through the ether oxygen) in which the alkyl group is unsubstituted or substituted as described below; Non-limiting examples of suitable alkoxy groups include methoxy, ethoxy, n-propoxy, isopropoxy, n-butoxy and heptoxy;

"Alkoxycarbonyl" means an alkyl-O—CO— group (i.e., the bond to the parent moiety is through the carbonyl) wherein the alkyl group is unsubstituted or substituted as previously defined; Non-limiting examples of suitable alkoxycarbonyl groups include methoxycarbonyl and ethoxycarbonyl;

"Alkyl" (including the alkyl portions of other moieties, such as trifluoroalkyl and alkyloxy) means an aliphatic hydrocarbon (chain) that can be straight or branched wherein said group comprises about 1 to about 20 carbon atoms in the chain; Preferred alkyl groups comprise about 1 to about 12 carbon atoms in the chain; More preferred alkyl groups comprise about 1 to about 6 carbon atoms in the chain; Branched means that one or more lower alkyl groups, such as methyl, ethyl or propyl, are attached to a linear alkyl chain; "Lower alkyl" means a group comprising about 1 to about 6 carbon atoms in the chain, and said chain can be straight or branched; The term "substituted alkyl" means that the alkyl group is substituted by one or more independently selected substituents, and wherein each substituent is independently selected from the group consisting of: halo, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl). Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl;

"Alkylaryl" means an alkyl-aryl- group (i.e., the bond to the parent moiety is through the aryl group) wherein the alkyl group is unsubstituted or substituted as defined above, and the aryl group is unsubstituted or substituted as defined below; Preferred alkylaryls comprise a lower alkyl group; Non-limiting examples of suitable alkylaryl groups include o-tolyl, p-tolyl and xylyl;

"Alkylheteroaryl" means an alkyl-heteroaryl- group (i.e., the bond to the parent moiety is through the heteroaryl group) wherein the alkyl is unsubstituted or substituted as defined above and the heteroaryl group is unsubstituted or substituted as defined below;

"Alkylsulfinyl" means an alkyl-S(O)— group (i.e., the bond to the parent moiety is through the sulfinyl) wherein the alkyl group is unsubstituted or substituted as previously defined; Preferred groups are those in which the alkyl group is lower alkyl;

"Alkylsulfonyl" means an alkyl-S(O$_2$)— group (i.e., the bond to the parent moiety is through the sulfonyl) wherein the alkyl group is unsubstituted or substituted as previously defined; Preferred groups are those in which the alkyl group is lower alkyl;

"Alkylthio" means an alkyl-S— group (i.e., the bond to the parent moiety is through the sulfur) wherein the alkyl group is unsubstituted or substituted as previously described; Non-limiting examples of suitable alkylthio groups include methylthio, ethylthio, i-propylthio and heptylthio;

"Alkynyl" means an aliphatic hydrocarbon group (chain) comprising at least one carbon to carbon triple bond, wherein the chain can be straight or branched, and wherein the group comprises about 2 to about 15 carbon atoms in the; Preferred alkynyl groups comprise about 2 to about 12 carbon atoms in the chain; and more preferably about 2 to about 4 carbon atoms in the chain; Branched means that one or more lower alkyl groups, such as methyl, ethyl or propyl, are attached to a linear alkynyl chain; "Lower alkynyl" means an alkynyl group comprising about 2 to about 6 carbon atoms in the chain, and the chain can be straight or branched; Non-limiting examples of suitable alkynyl groups include ethynyl, propynyl, 2-butynyl, 3-methylbutynyl, n-pentynyl, and decynyl; The term "substituted alkynyl" means that the alkynyl group is substituted by one or more independently selected, and each substituent is independently selected from the group consisting of alkyl; aryl and cycloalkyl;

"Amino" means an —NH$_2$ group;

"Aralkenyl" means an aryl-alkenyl- group (i.e., the bond to the parent moiety is through the alkenyl group) wherein the aryl group is unsubstituted or substituted as defined previously, and the alkenyl group is unsubstituted or substituted as defined previously; Preferred aralkenyls contain a lower alkenyl group; Non-limiting examples of suitable aralkenyl groups include 2-phenethenyl and 2-naphthylethenyl;

"Aralkoxycarbonyl" means an aralkyl-O—C(O)— group (i.e., the bond to the parent moiety is through the carbonyl) wherein the aralkyl group is unsubstituted or substituted as previously defined; A non-limiting example of a suitable aralkoxycarbonyl group is benzyloxycarbonyl;

"Aralkyloxy" means an aralkyl-O— group (i.e., the bond to the parent moiety is through the ether oxygen) wherein the aralkyl group is unsubstituted or substituted as previously described; Non-limiting examples of suitable aralkyloxy groups include benzyloxy and 1- or 2-naphthalenemethoxy;

"Aralkyl" or "arylalkyl" means an aryl-alkyl- group (i.e., the bond to the parent moiety is through the alkyl group) wherein the aryl is unsubstituted or substituted as defined below and the alkyl is unsubstituted or substituted as defined above; Preferred aralkyls comprise a lower alkyl group. Non-limiting examples of suitable aralkyl groups include benzyl, 2-phenethyl and naphthalenylmethyl;

"Aralkylthio" means an aralkyl-S— group (i.e., the bond to the parent moiety is through the sulfur) wherein the aralkyl group is unsubstituted or substituted as previously described; A non-limiting example of a suitable aralkylthio group is benzylthio;

"Aroyl" means an aryl-C(O)— group (i.e., the bond to the parent moiety is through the carbonyl) wherein the aryl group is unsubstituted or substituted as defined below; Non-limiting examples of suitable groups include benzoyl and 1- and 2-naphthoyl;

"Aryl" (sometimes abbreviated "ar") means an aromatic monocyclic or multicyclic ring system comprising about 6 to about 14 carbon atoms, preferably about 6 to about 10 carbon atoms; The aryl group can be optionally substituted with one or more independently selected "ring system substituents" (defined below). Non-limiting examples of suitable aryl groups include phenyl and naphthyl;

"arylalkyl" (or "aralkyl") means an aryl-alkyl- group (i.e., the bond to the parent moiety is through the alkyl group) wherein the aryl and alkyl groups are unsubstituted or substituted as defined above;

"Aryloxy" means an aryl-O— group (i.e., the bond to the parent moiety is through the ether oxygen) wherein the aryl group is unsubstituted or substituted as defined above; Non-limiting examples of suitable aryloxy groups include phenoxy and naphthoxy;

"Aryloxycarbonyl" means an aryl-O—C(O)— group (i.e., the bond to the parent moiety is through the carbonyl) wherein the aryl group is unsubstituted or substituted as previously defined; Non-limiting examples of suitable aryloxycarbonyl groups include phenoxycarbonyl and naphthoxycarbonyl;

"Arylsulfinyl" means an aryl-S(O)— group (i.e., the bond to the parent moiety is through the sulfinyl) wherein aryl is unsubstituted or substituted as previously defined;

"Arylsulfonyl" means an aryl-S($O_2$)— group (i.e., the bond to the parent moiety is through the sulfonyl) wherein aryl is unsubstituted or substituted as previously defined;

"Arylthio" means an aryl-S— group (i.e., the bond to the parent moiety is through the sulfur) wherein the aryl group is unsubstituted or substituted as previously described; Non-limiting examples of suitable arylthio groups include phenylthio and naphthylthio;

"Cycloalkenyl" means a non-aromatic mono or multicyclic ring system comprising about 3 to about 10 carbon atoms, preferably about 5 to about 10 carbon atoms that contains at least one carbon-carbon double bond; Preferred cycloalkenyl rings contain about 5 to about 7 ring atoms; The cycloalkenyl can be optionally substituted with one or more independently selected "ring system substituents" (defined below); Non-limiting examples of suitable monocyclic cycloalkenyls include cyclopentenyl, cyclohexenyl, cycloheptenyl, and the like; A non-limiting example of a suitable multicyclic cycloalkenyl is norbornylenyl;

"Cycloalkyl" means a non-aromatic mono- or multicyclic ring system comprising about 3 to about 10 carbon atoms, preferably about 5 to about 10 carbon atoms; Preferred cycloalkyl rings contain about 5 to about 7 ring atoms; The cycloalkyl can be optionally substituted with one or more independently selected "ring system substituents" (defined below); Non-limiting examples of suitable monocyclic cycloalkyls include cyclopropyl, cyclopentyl, cyclohexyl, cycloheptyl and the like; Non-limiting examples of suitable multicyclic cycloalkyls include 1-decalin, norbornyl, adamantyl and the like;

"Cycloalkylalkyl" means a cycloalkyl-alkyl- group (i.e., the bond to the parent moiety is through the alkyl group) wherein the cycloalkyl group and the alkyl group are unsubstituted or substituted as defined above;

"Halo" means fluoro, chloro, bromo, or iodo groups; Preferred halos are fluoro, chloro or bromo;

"Halogen" means fluorine, chlorine, bromine, or iodine; Preferred halogens are fluorine, chlorine and bromine;

"Haloalkyl" means an alkyl, as defined above, wherein one or more hydrogen atoms on the alkyl is replaced by a halo group, as defined above;

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; Preferred heteroaryls comprise about 5 to about 6 ring atoms; The "heteroaryl" can be optionally substituted by one or more independently selected "ring system substituents" (defined below); The prefix aza, oxa or thia before the heteroaryl root name means that at least a nitrogen, oxygen or sulfur atom, respectively, is present as a ring atom; A nitrogen atom of a heteroaryl can be optionally oxidized to the corresponding N-oxide; Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like;

"Heteroaralkyl" means a heteroaryl-alkyl- group (i.e., the bond to the parent moiety is through the alkyl group) in which the heteroaryl is unsubstituted or substituted as defined above, and the alkyl group is unsubstituted or substituted as defined above; Preferred heteroaralkyls comprise an alkyl group that is a lower alkyl group; Non-limiting examples of suitable aralkyl groups include pyridylmethyl, 2-(furan-3-yl) ethyl and quinolin-3-ylmethyl;

"Heteroaralkylthio" means a heteroaralkyl-S— group wherein the heteroaralkyl group is unsubstituted or substituted as defined above;

"Heteroarylsulfinyl" means a heteroaryl-SO— group wherein the heteroaryl group is unsubstituted or substituted as defined above;

"Heteroarylsulfonyl" means a heteroaryl-$SO_2$— group wherein the heteroaryl group is unsubstituted or substituted as defined above;

"Heteroarylthio" means a heteroaryl-S— group wherein the heteroaryl group is unsubstituted or substituted as defined above;

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; There are no adjacent oxygen and/or sulfur atoms present in the ring system; Preferred heterocyclenyl rings contain about 5 to about 6 ring atoms; The prefix aza, oxa or thia before the heterocyclenyl root name means that at least a nitrogen, oxygen or sulfur atom, respectively, is present as a ring atom; The heterocyclenyl can be optionally substituted by one or more independently selected "Ring system substituents" (defined below); The nitrogen or sulfur atom of the heterocyclenyl can be optionally oxidized to the corresponding N-oxide, S-oxide or S,S-dioxide; Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like; Non-limiting examples of suitable oxaheterocyclenyl groups include 3,4-dihydro-2H-pyran, dihydrofuranyl, fluorodihydrofuranyl, and the like; A non-limiting example of a suitable multicyclic oxaheterocyclenyl group is 7-oxabicyclo[2.2.1]heptenyl; Non-limiting examples of suitable monocyclic thiaheterocyclenyl rings include dihydrothiophenyl, dihydrothiopyranyl, and the like;

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; There are no adjacent oxygen and/or sulfur atoms present in the ring system; Preferred heterocyclyls contain about 5 to about 6 ring atoms; The prefix aza, oxa or thia before the heterocyclyl root name means that at least a nitrogen, oxygen or sulfur atom respectively is present as a ring atom; The heterocyclyl can be optionally substituted by one or more independently selected "ring system substituents" (defined below); The nitrogen or sulfur atom of the heterocyclyl can be optionally oxidized to the corresponding N-oxide, S-oxide or S,S-dioxide; Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like;

"Hydroxyalkyl" means a HO-alkyl- group wherein the alkyl group is substituted or unsubstituted as defined above; Preferred hydroxyalkyls comprise a lower alkyl; Non-limiting examples of suitable hydroxyalkyl groups include hydroxymethyl and 2-hydroxyethyl;

"Ring system substituent" means a substituent attached to an aromatic or non-aromatic ring system that, for example, replaces an available hydrogen on the ring system; Ring system substituents are each independently selected from the group consisting of: alkyl, alkenyl, alkynyl, aryl, heteroaryl, aralkyl, alkylaryl, aralkenyl, heteroaralkyl, alkylheteroaryl, heteroaralkenyl, heteroarylalkynl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—Y$_1$Y$_2$NSO$_2$—, and —SO$_2$NY$_1$Y$_2$, wherein Y$_1$ and Y$_2$ are each independently selected from the group consisting of: hydrogen, alkyl, aryl, cycloalkyl, and aralkyl; "Ring system substituent" also means a single moiety which simultaneously replaces two available hydrogens on two adjacent carbon atoms (one H on each carbon) on a ring system, examples of such moieties include methylene dioxy, ethylenedioxy, —C(CH$_3$)$_2$— and the like that form moieties such as, for example:

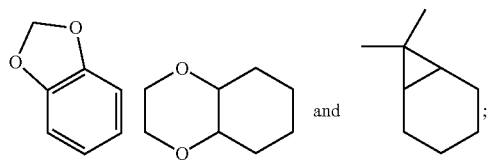

"Ring system substituent" also means a cyclic ring of 3 to 7 ring atoms, wherein 1-2 ring atoms can be heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring; Non-limiting examples include:

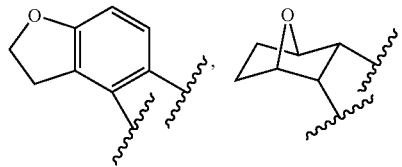 and the like;

and

It should be noted that in hetero-atom containing heterocyclyl ring systems of this invention, there are no hydroxyl groups on carbon atoms adjacent to a N, O or S, as well as there are no N or S groups on carbon adjacent to another heteroatom, Thus, for example, in the ring:

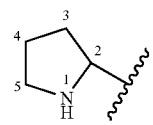

there is no —OH attached directly to carbons marked 2 and 5.

It should also be noted that tautomeric forms such as, for example, the moieties:

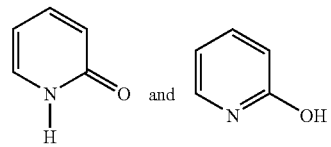

are considered equivalent in certain embodiments of this invention.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., $R^1$, $R^2$, etc.) occurs more than one time in any constituent or in Formula 1.0, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The positions in the tricyclic ring system are:

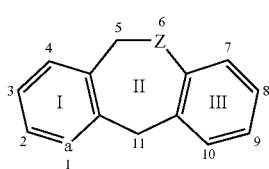

The compounds of formula 1.0 include the 2R and 2S isomers shown below (2R is preferred):

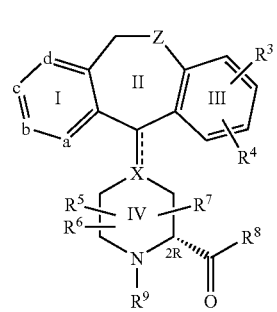

(1.0A)

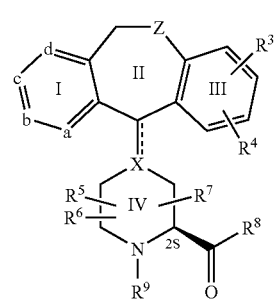

(1.0B)

Examples of the optional substituents for the $R^{12}$ or $R^{12A}$ moiety include: —$CH_3$, —$CH_2OH$, —$CH_2OC(O)O$-cyclohexyl, —$CH_2OC(O)O$-cyclopentyl, ethyl, isopropyl, $NH_2$, and —$NHC(O)CF_3$.

Examples of $R^{17}$ include: —$C(O)NH$-cyclohexyl, —$C(phenyl)_3$, H, methyl or ethyl.

Examples of $R^{20}$ include t-butyl, i-propyl, neopentyl, cyclohexyl, cyclopropylmethyl,

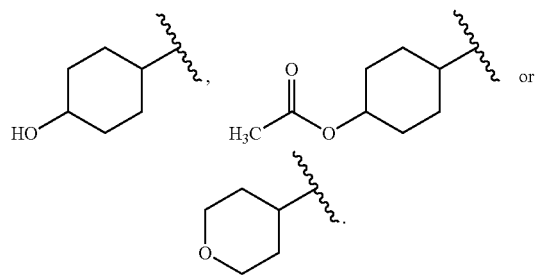

Examples of $R^{20}$ for group 12.0 include: t-butyl, ethyl, benzyl, —$CH(CH_3)_2$, —$CH_2CH(CH_3)_2$, —$(CH_2)_2CH_3$, n-butyl, n-hexyl, n-octyl, p-chlorophenyl, cyclohexyl, cyclopentyl, neopentyl, cyclopropylmethyl or

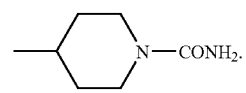

Examples of $R^{20}$ and $R^{21}$ for 13.0 include: cyclohexyl, t-butyl, H, —$CH(CH_3)_2$, ethyl, —$(CH_2)_2CH_3$, phenyl, benzyl, —$(CH_2)_2$phenyl, and —$CH_3$.

Examples of $R^{20}$ for 14.0 include: 4-pyridylNO, —$OCH_3$, —$CH(CH_3)_2$, -t-butyl, H, propyl, cyclohexyl and

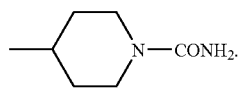

Examples for $R^{22}$ for 15.0 include: t-butyl, cyclohexyl, cyclopentyl, cyclobutyl, cyclopropyl, cyclopropylmethyl, phenyl, substituted phenyl (e.g., halo, such as F or Cl),

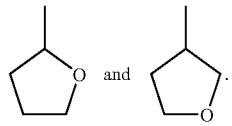

Examples for $R^{20}$ for 16.0 include: methyl, phenyl, isopropyl and cyclohexylmethyl.

Examples of $R^{13}$ and $R^{14}$ include: H, F, phenyl, —$CH_3$, —$CH_2CH(CH_3)_2$, —$(CH_2)_3CH_3$, benzyl, ethyl, p-chlorophenyl, and —OH (provided that that there can only be one OH on each carbon).

Cyclopropyl is an Example of the $R^{13}$ and $R^{14}$ group being taken together with the carbon atom to which they are bound to form a cycloalkyl ring.

$R^1$, $R^2$, $R^3$, and $R^4$ are preferably selected from H and halo, and are more preferably selected from H, Br, F and Cl. Representative compounds of formula 1.0 include trihalo, dihalo and monohalo substituted compounds, such as, for example: (1) 3,8,10-trihalo; (2) 3,7,8-trihalo; (3) 3,8-dihalo; (4) 8-halo; (5) 10-halo; and (6) 3-halo (i.e., no substituent in Ring III) substituted compounds; wherein each halo is independently selected. Preferred compounds of formula 1.0 include: (1) 3-Br-8-Cl-10-Br-substituted compounds; (2) 3-Br-7-Br-8-Cl-substituted compounds; (3) 3-Br-8-Cl-substituted compounds; (4) 3-Cl-8-Cl-substituted compounds; (5) 3-F-8-Cl-substituted compounds; (6) 8-Cl-substituted compounds; (7) 10-Cl-substituted compounds; (8) 3-Cl-substituted compounds; (9) 3-Br-substituted compounds; and (10) 3-F-substituted compounds.

Substituent a is preferably N or $N^+O^-$ with N being preferred.

Z is selected from the group consisting of: —O—, —S—, —S(O)—, —S(O$_2$)—, and —N($R^{10}$)—

$R^5$, $R^6$, and $R^7$ are preferably H.

X is preferably N or CH (i.e., the optional bond is absent), and more preferably X is N.

When one or more of the carbon atoms of the imidazole ring 8.0 or 9.0 are substituted, the substituents are generally selected from: —N($R^{15}$)$_2$, —NHC(O)$R^{15}$, —C($R^{18}$)$_2$OR$^{19}$, or alkyl, e.g., —$CH_3$, —$CH_2OH$, —$CH_2OC(O)O$-cyclohexyl, —$CH_2OC(O)O$-cyclopentyl, ethyl, isopropyl, $NH_2$, or —NHC(O)CF$_3$.

$R^{17}$ is preferably H or alkyl, most preferably H, methyl or ethyl, and more preferably methyl.

$R^{20}$ in substituent 12.0 is preferably selected from: alkyl or cycloalkyl, most preferably t-butyl, isopropyl, neopentyl, cyclohexyl or cyclopropylmethyl.

$R^{20}$ in substituent 13.0 is preferably selected from: alkyl or cycloalkyl; most preferably t-butyl, isopropyl or cyclohexyl. $R^{21}$ is preferably selected from: H or alkyl; most preferably H, methyl or isopropyl; and more preferably H.

$R^{20}$ in substituent 14.0 is preferably selected from: cycloalkyl or alkyl.

$R^{22}$ in substituent 15.0 is preferably selected from: phenyl, cyclopropyl, cyclobutyl, cyclopentyl, cyclohexyl, t-butyl, cyclopropylmethyl,

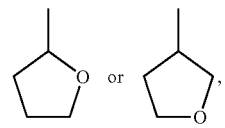

and most preferably selected from: t-butyl, cyclopropyl, cyclobutyl, cyclopentyl or cyclohexyl.

$R^{20}$ in substituent 16.0 is preferably selected from: alkyl or cycloalkylalkyl; most preferably methyl, isopropyl or cyclohexylmethyl; more preferably methyl or isopropyl; and even more preferably methyl.

$R^{13}$ and $R^{14}$ are preferably selected from: H, F, $C_1$ to $C_4$ alkyl (e.g., methyl or isopropyl), —CON($R^{15}$)$_2$ (e.g., —CONH$_2$), —OR$^{15}$ (e.g., —OH), aryl (e.g., phenyl) or arylalkyl (e.g., benzyl); or when $R^{13}$ and $R^{14}$ are taken together to form a cycloalkyl ring, said ring is preferably cyclopropyl cyclopentyl or cyclohexyl. Most preferably $R^{13}$ and $R^{14}$ are H.

For compounds of the invention, n is preferably 1-3, most preferably 1-2.

For compounds wherein $R^8$ is ring 2.0 or 7.0, the —(CR$^{13}R^4$)$_n$—R$^{12}$ substituent can be in the 2-, 3- or 4-position relative to the ring nitrogen, provided that the —(CR$^{13}R^{14}$)$_n$—R$^{12}$ substituent is not in the 4-position when Y is O, S, SO or SO$_2$. Preferably, the —(CR$^{13}R^{14}$)$_n$—R$^{12}$ substituent is in the 2- or 3-position, and most preferably in the 3-position. More preferably, the —(CR$^{13}R^{14}$)$_n$—R$^{12}$ substituent is in the 2-position when n is 2, and in the 3-position when n is 1.

Compounds of formula 1.0, wherein X is N or CH, include, with reference to the C-11 bond, the R- and S-isomers:

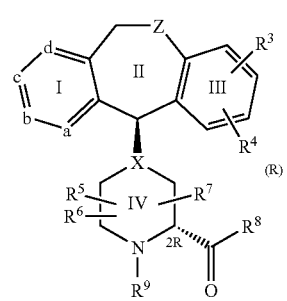

(17.0)

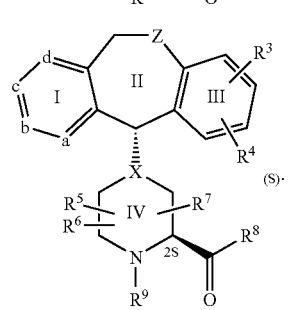

(18.0)

Compounds of this invention include the C-11 R- and S-isomers having the 2S stereochemistry.

Thus, one embodiment of this invention is directed to compounds of formula 1.0 having the formula 1.0A:

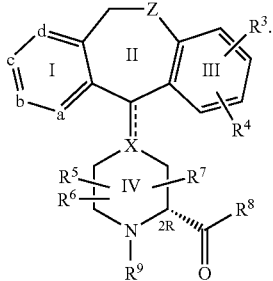

(1.0A)

Another embodiment of this invention is directed to compounds of formula 1.0 having the formula 1.0B:

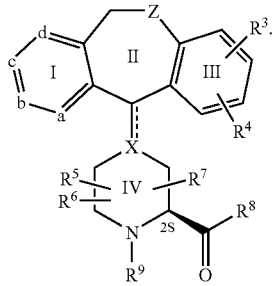

(1.0B)

Another embodiment of this invention is directed to compounds of formula 1.0 wherein $R^1$ to $R^4$ are independently selected from the group consisting of: H, Br, F and Cl; $R^5$ to $R^7$ are H; a is N and the remaining b, c and d substituents are carbon; and Z is: —O—.

Another embodiment of this invention is directed to compounds of formula 1.0 wherein $R^8$ is selected from the group consisting of:

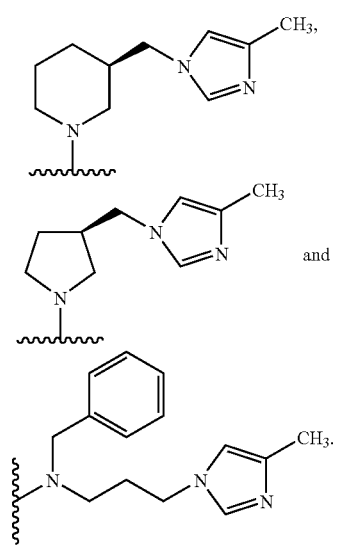

Another embodiment of this invention is directed to compounds of formula 1.0 wherein $R^{13}$ and $R^{14}$ are H.

Another embodiment of this invention is directed to compounds of formula 1.0 wherein Y is selected from the group consisting of: —S—, —S(O)—, and —S(O$_2$)—.

Another embodiment of this invention is directed to compounds of formula 1.0 wherein Y is —O—.

Another embodiment of this invention is directed to compounds of formula 1.0 wherein Y is —NR$^{16}$—.

Another embodiment of this invention is directed to compounds of formula 1.0 wherein $R^9$ is group 12.0.

Another embodiment of this invention is directed to compounds of formula 1.0 wherein $R^9$ is group 13.0.

Another embodiment of this invention is directed to compounds of formula 1.0 wherein $R^9$ is group 15.0.

Another embodiment of this invention is directed to compounds of formula 1.0 wherein $R^1$ to $R^4$ are independently selected from the group consisting of: H, Br, F and Cl; $R^5$ to $R^7$ are H, a is N and the remaining b, c and d substituents are carbon; Z is —O—; and Y is CH$_2$.

Another embodiment of this invention is directed to compounds of formula 1.0 wherein $R^1$ to $R^4$ are independently selected from the group consisting of: H, Br, F and Cl; $R^5$ to $R^7$ are H, a is N and the remaining b, c and d substituents are carbon; Z is —O—; Y is CH$_2$; and $R^{13}$ and $R^{14}$ are H.

Another embodiment of this invention is directed to compounds of formula 1.0 wherein $R^1$ to $R^4$ are independently selected from the group consisting of: H, Br, F and Cl; $R^5$ to $R^7$ are H, a is N and the remaining b, c and d substituents are carbon; Z is —O—; Y is CH$_2$; $R^{13}$ and $R^{14}$ are H; and $R^{12}$ is 9.0.

Another embodiment of this invention is directed to compounds of formula 1.0 wherein $R^1$ to $R^4$ are independently selected from the group consisting of: H, Br, F and Cl; $R^5$ to $R^7$ are H, a is N and the remaining b, c and d substituents are carbon; Z is —O—; Y is CH$_2$; $R^{13}$ and $R^{14}$ are H; and $R^9$ is 13.0.

Another embodiment of this invention is directed to compounds of formula 1.0 wherein $R^1$ to $R^4$ are independently selected from the group consisting of: H, Br, F and Cl; $R^5$ to $R^7$ are H, a is N and the remaining b, c and d substituents are carbon; Z is —O—; Y is CH$_2$; $R^{13}$ and $R^{14}$ are H; and $R^9$ is 15.0.

Another embodiment of this invention is directed to compounds of formula 1.0 wherein $R^1$ to $R^4$ are independently selected from the group consisting of: H, Br, F and Cl; $R^5$ to $R^7$ are H, a is N and the remaining b, c and d substituents are carbon; Z is —O—; Y is CH$_2$; $R^{13}$ and $R^{14}$ are H; and $R^{20}$ is selected from the group consisting of t-butyl, i-propyl, neopentyl, cyclohexyl, and cyclopropylmethyl.

Another embodiment of this invention is directed to compounds of formula 1.0 wherein $R^1$ to $R^4$ are independently selected from the group consisting of: H, Br, F and Cl; $R^5$ to $R^7$ are H, a is N and the remaining b, c and d substituents are carbon; Z is —O—; Y is CH$_2$; $R^{13}$ and $R^{14}$ are H; and $R^9$ is selected from the group consisting of: 12.0 and 13.0, and $R^{21}$ for 13.0 is H.

Representative compounds of this invention include, but are not limited to:

(1.1)
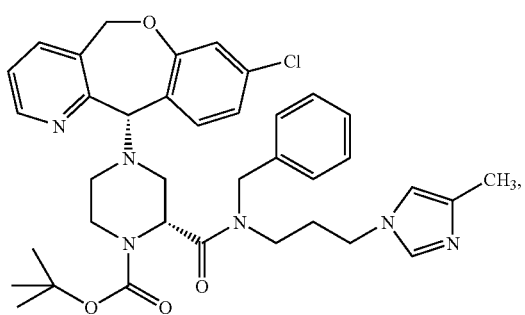
(1.2)
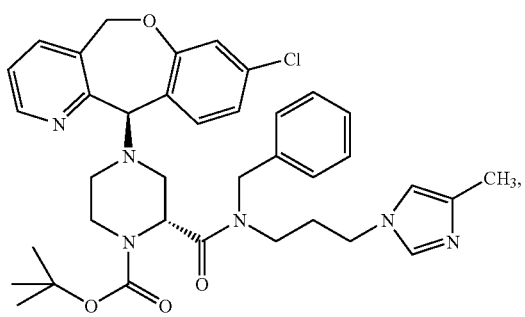
(1.3)
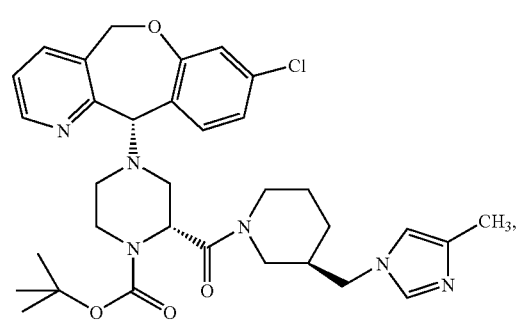
(1.4)
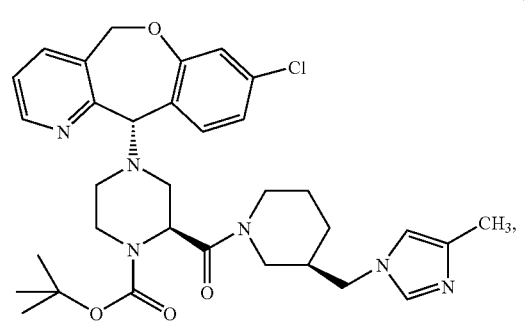
-continued
(1.5)
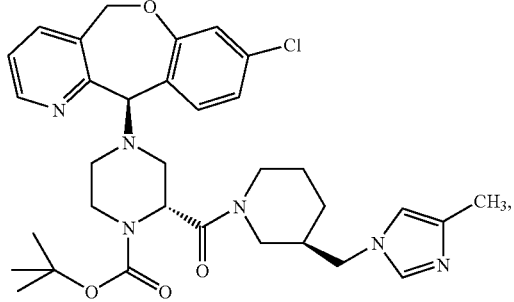
(1.6)
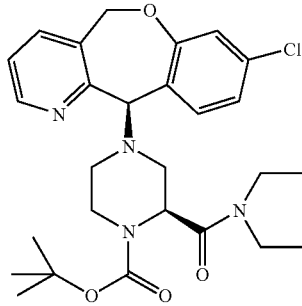
(1.7)
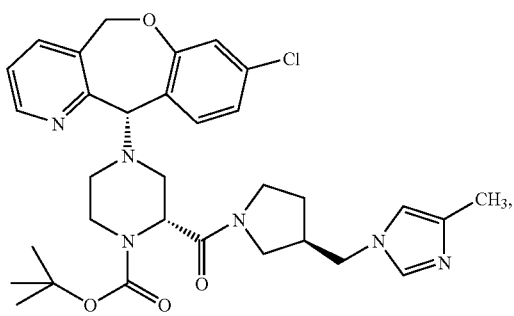
(1.8)
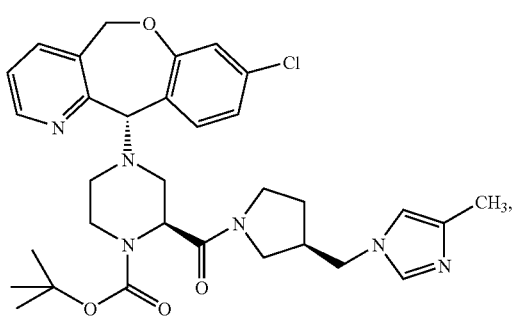

-continued

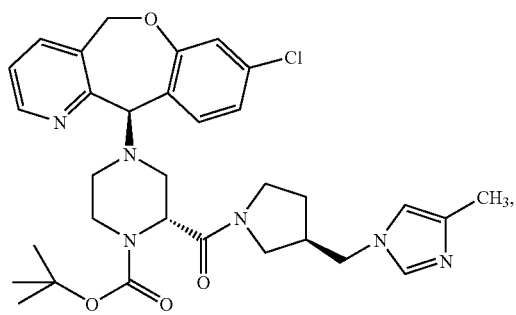

(1.9)

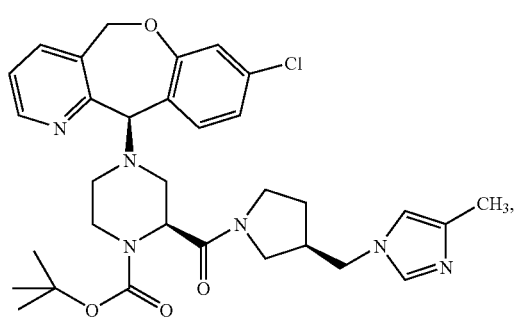

(1.10)

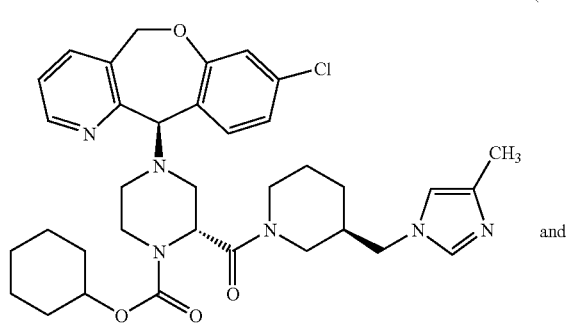

(1.11)

and

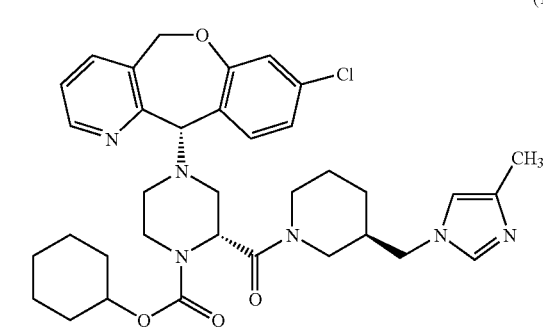

(1.12)

Thus, another embodiment of this invention is directed to compounds 1.1 to 1.12 (i.e., the final compounds of Examples 1 to 12).

Another embodiment of this invention is directed to compounds 1.1 to 1.9 (i.e., the final compounds of Examples 1 to 9).

Another embodiment of this invention is directed to compounds 1.1 to 1.6 and 1.8 (i.e., the final compounds of Examples 1 to 6 and 8).

Another embodiment of this invention is directed to compounds 1.1 to 1.6 (i.e., the final compounds of Examples 1 to 6).

Another embodiment of this invention is directed to compounds 1.2 to 1.6 (i.e., the final compounds of Examples 2 to 6).

Another embodiment of this invention is directed to compounds 1.2 to 1.4 and 1.6 (i.e., the compounds of Examples 2 to 4 and 6).

Another embodiment of this invention is directed to compound 1.1.

Another embodiment of this invention is directed to compound 1.2.

Another embodiment of this invention is directed to compound 1.3.

Another embodiment of this invention is directed to compound 1.4.

Another embodiment of this invention is directed to compound 1.5.

Another embodiment of this invention is directed to compound 1.6.

Another embodiment of this invention is directed to compound 1.7.

Another embodiment of this invention is directed to compound 1.8.

Another embodiment of this invention is directed to compound 1.9.

Another embodiment of this invention is directed to compound 1.10.

Another embodiment of this invention is directed to compound 1.11.

Another embodiment of this invention is directed to compound 1.12.

Lines drawn into the ring systems indicate that the indicated bond may be attached to any of the substitutable ring carbon atoms of any ring when more than one ring is present (e.g., ring 5.0).

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1.0 or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

The compounds of formula 1.0 can form salts that are also within the scope of this invention. Reference to a compound of formula 1.0 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula 1.0 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the formula 1.0 may be formed, for example, by reacting a compound of formula 1.0 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

One or more compounds of the invention can also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

Compounds of formula 1.0, and salts, solvates and prodrugs thereof, may exist in their tautomeric form (for example, as an amide or imino ether). All such tautomeric forms are contemplated herein as part of the present invention.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

This invention also includes the compounds of this invention in isolated and purified form.

Polymorphic forms of the compounds of formula 1.0, and of the salts, solvates and prodrugs of the compounds of formula 1.0, are intended to be included in the present invention.

This invention provides a method for inhibiting or treating the abnormal growth of cells, including transformed cells, by administering an effective amount (e.g., a therapeutically effective amount) of one or more (e.g., one) compounds of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor (i.e., cancer) growth by administering an effective amount (e.g., a therapeutically effective amount) of one or more (e.g., one) compounds of this invention to a patient in need of such treatment. In particular, this invention provides a method for inhibiting or treating the growth of tumors expressing an activated Ras oncogene by the administration of an effective amount (e.g., a therapeutically effective amount) of one or more (e.g., one) compounds of this invention.

The present invention also provides a method of treating proliferative diseases, especially cancers (i.e., tumors), comprising administering an effective amount (e.g., a therapeutically effective amount) of one or more (e.g., one) compounds of the invention, described herein, to a mammal (e.g., a human) in need of such treatment in combination with an effective amount of at least one anti-cancer agent (i.e., a chemotherapeutic agent) and/or radiation.

Examples of anti-cancer agents (i.e., chemotherapeutic agents) include anti-cancer agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) small molecules that are inhibitors of αVβ3 integrins, (14) folate antagonists, (15) ribonucleotide reductase inhibitors, (16) anthracyclines, (17) biologics; (18) thalidomide (or related imid), and (19) Gleevec.

The present invention also provides a method of treating proliferative diseases, particularly cancers (i.e., tumors), comprising administering an effective amount (e.g., a therapeutically effective amount) of one or more (e.g., one) compounds of the invention to a mammal (e.g., a human) in need of such treatment in combination With an effective amount of at least one signal transduction inhibitor.

Examples of proliferative diseases (e.g., tumors, i.e., cancers) that may be inhibited or treated include, but are not limited to:
(A) Lung cancer (e.g., lung adenocarcinoma and non small cell lung cancer);
(B) Pancreatic cancers (e.g., pancreatic carcinoma such as, for example, exocrine pancreatic carcinoma);
(C) Colon cancers (e.g., colorectal carcinomas, such as, for example, colon adenocarcinoma and colon adenoma);
(D) Myeloid leukemias (for example, acute myelogenous leukemia (AML), CML, and CMML);
(E) Thyroid follicular cancer;
(F) Myelodysplastic syndrome (MDS);
(G) Bladder carcinoma;
(H) Epidermal carcinoma;
(I) Melanoma;
(J) Breast cancer;
(K) Prostate cancer;
(L) Head and neck cancers (e.g., squamous cell cancer of the head and neck);
(M) Ovarian cancer;
(N) Brain cancers (e.g., gliomas);
(O) Cancers of mesenchymal origin (e.g., fibrosarcomas and rhabdomyosarcomas);
(P) Sarcomas;
(O) Tetracarcinomas;
(R) Nuroblastomas;
(S) Kidney carcinomas;
(T) Hepatomas;
(U) Non-Hodgkin's lymphoma;
(V) Multiple myeloma; and
(W) Anaplastic thyroid carcinoma.

For example, embodiments of this invention include methods of treating cancer, wherein said cancer is selected from the group consisting of: pancreatic cancers, lung cancers, myeloid leukemias, thyroid follicular tumors, myelodysplastic syndrome, head and neck cancers, melanomas, breast cancers, prostate cancers, ovarian cancers, bladder cancers, gliomas, epidermal cancers, colon cancers, non-Hodgkin's lymphomas, and multiple myelomas, comprising administering to said patient in need of such treatment, an effective amount of one or more (e.g., one) compounds of this invention.

Also for example, embodiments of this invention include methods of treating cancer, wherein said cancers are selected from the group consisting of: lung cancer (e.g., non-small cell lung cancer), head and neck cancer (e.g., squamous cell cancer of the head and neck), bladder cancer, breast cancer, prostate cancer, and myeloid leukemias (e.g., CML and AML), non-Hodgkin's lymphoma and multiple myeloma, comprising administering to said patient in need of such treatment, an effective amount of one or more (e.g., one) compounds of this invention.

This invention also provides a method of treating cancer in a patient in need of such treatment comprising administering to said patient a therapeutically effective amount of one or more (e.g., one) compounds of this invention and therapeutically effective amounts of at least two different antineoplastic agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) small molecules that are inhibitors of αVβ3 integrins, (14) folate antagonists, (15) ribonucleotide reductase inhibitors, (16) anthracyclines, (17) biologics; (18) thalidomide (or related imid), and (19) Gleevec.

This invention also provides a method of treating cancer in a patient in need of such treatment comprising administering to said patient therapeutically effective amounts of one or more (e.g., one) compounds of this invention and an antineoplastic agent selected from the group consisting of: (1) EGF inhibitors that are antibodies, (2) EGF inhibitors that are small molecules, (3) VEGF inhibitors that are antibodies, and (4) VEGF inhibitors that are small molecules. Radiation therapy can also be used in conjunction with the above combination therapy, i.e., the above method using a combination of compounds of the invention and antineoplastic agent can also comprise the administration of a therapeutically effect amount of radiation.

This invention also provides a method of treating leukemias (e.g., acute myeloid leukemia (AML), and chronic myeloid leukemia (CML)) in a patient in need of such treatment comprising administering to said patient therapeutically effective amounts of one or more (e.g., one) compounds of this invention and: (1) Gleevec and interferon to treat CML; (2) Gleevec and pegylated interferon to treat CML; (3) an anti-tumor nucleoside derivative (e.g., Ara-C) to treat AML; or (4) an anti-tumor nucleoside derivative (e.g., Ara-C) in combination with an anthracycline to treat AML.

This invention also provides a method of treating non-Hodgkin's lymphoma in a patient in need of such treatment comprising administering to said patient therapeutically effective amounts of one or more (e.g., one) compounds of this invention and: (1) a biologic (e.g., Rituxan); (2) a biologic (e.g., Rituxan) and an anti-tumor nucleoside derivative (e.g., Fludarabine); or (3) Genasense (antisense to BCL-2).

This invention also provides a method of treating multiple myeloma in a patient in need of such treatment comprising administering to said patient therapeutically effective amounts of one or more (e.g., one) compounds of this invention and: (1) a proteosome inhibitor (e.g., PS-341 from Millenium); or (2) Thalidomide (or related imid).

This invention also provides a method of treating cancer, said treatment comprising administering to a patient in need of such treatment therapeutically effective amounts of:
(a) One or more (e.g., one) compounds of this invention;
(b) At least two different antineoplastic agents selected from the group consisting of: (1) taxanes; (2) platinum coordinator compounds; (3) EGF inhibitors that are antibodies; (4) EGF inhibitors that are small molecules; (5) VEGF inhibitors that are antibodies; (6) VEGF kinase inhibitors that are small molecules; (7) estrogen receptor antagonists or selective estrogen receptor modulators; (8) anti-tumor nucleoside derivatives; (9) epothilones; (10) topoisomerase inhibitors; (11) vinca alkaloids; (12) antibodies that are inhibitors of αVβ3 integrins; (13) small molecule inhibitors of αVβ3 integrins (14) folate antagonists; (15) ribonucleotide reductase inhibitors; (16) anthracyclines; (17) biologics; and (18) Thalidomide (or related Imid).

This invention also provides a method of treating cancer, said treatment comprising administering to a patient in need of such treatment therapeutically effective amounts of:
(a) One or more (e.g., one) compounds of this invention;
(b) At least two different antineoplastic agents selected from the group consisting of: (1) taxanes; (2) platinum coordinator compounds; (3) EGF inhibitors that are antibodies; (4) EGF inhibitors that are small molecules; (5) VEGF inhibitors that are antibodies; (6) VEGF kinase inhibitors that are small molecules; (7) estrogen receptor antagonists or selective estrogen receptor modulators; (8) anti-tumor nucleoside derivatives; (9) epothilones; (10) topoisomerase inhibitors; (11) vinca alkaloids; (12) antibodies that are inhibitors of αVβ3 integrins; or (13) small molecule inhibitors of αVβ3 integrins (14) folate antagonists; (15) ribonucleotide reductase inhibitors; (16) anthracyclines; and (17) biologics.

This invention also provides a method of treating cancer, said treatment comprising administering to a patient in need of such treatment therapeutically effective amounts of:
(a) One or more (e.g., one) compounds of this invention;
(b) At least two different antineoplastic agents selected from the group consisting of: (1) taxanes; (2) platinum coordinator compounds; (3) EGF inhibitors that are antibodies; (4) EGF inhibitors that are small molecules; (5) VEGF inhibitors that are antibodies; (6) VEGF kinase inhibitors that are small molecules; (7) estrogen receptor antagonists or selective estrogen receptor modulators; (8) anti-tumor nucleoside derivatives; (9) epothilones; (10) topoisomerase inhibitors; (11) vinca alkaloids; (12) antibodies that are inhibitors of αVβ3 integrins; and (13) small molecule inhibitors of αVβ3 integrins.

Antineoplastic agents that can be used in combination with the FPT inhibitors (i.e., the compounds of this invention) are:
(1) Taxanes such as paclitaxel (TAXOL®) and/or docetaxel (Taxotere®);
(2) Platinum coordinator compounds, such as, for example, carboplatin, cisplatin and oxaliplatin;
(3) EGF inhibitors that are antibodies, such as: HER2 antibodies (such as, for example trastuzumab (Herceptin®), Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), Cl 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);
(4) EGF inhibitors that are small molecules, such as, Tarceva (TM) (OSI-774, OSI Pharmaceuticals, Inc.), and Iressa (ZD 1839, Astra Zeneca);
(5) VEGF inhibitors that are antibodies such as: bevacizumab (Genentech, Inc.), and IMC-1 C11 (ImClone Systems), DC 101 (a KDR VEGF Receptor 2 from ImClone Systems);
(6) VEGF kinase inhibitors that are small molecules such as SU 5416 and SU 6688 (both from Sugen, Inc.);
(7) Estrogen Receptor Antagonists or Selective Estrogen Receptor Modulators (SERMs), such as tamoxifen, idoxifene, raloxifene, trans-2,3-dihydroraloxifene, levormeloxifene, droloxifene, MDL 103,323, and acolbifene (Schering Corp.);
(8) Anti-tumor nucleoside derivatives such as 5-fluorouracil, gemcitabine or capecitabine;
(9) Epothilones such as BMS-247550 (Bristol-Myers Squibb), and EPO906 (Novartis Pharmaceuticals);
(10) Topoisomerase inhibitors such as topotecan (Glaxo SmithKline), and Camptosar (Pharmacia);
(11) Vinca alkaloids, such as, navelbine (Anvar and Fabre, France), vincristine and vinblastine; and
(12) Antibodies that are inhibitors of αVβ3 integrins, such as, LM-609 (see, Clinical Cancer Research, Vol. 6, page 3056-3061, August 2000, the disclosure of which is incorporated herein by reference thereto).

Preferred antineoplastic agents are selected from: paclitaxel, docetaxel, carboplatin, cisplatin, gemcitabine, tamoxifen, Herceptin, Cetuximab, Tarceva, Iressa, bevacizumab, navelbine, IMC-1C11, SU5416 or SU6688. Most preferred antineoplastic agents are selected from: paclitaxel, docetaxel, carboplatin, cisplatin navelbine, gemcitabine, or Herceptin.

This invention also provides a method of treating cancer, said treatment comprising administering to a patient in need of such treatment therapeutically effective amounts of:
(a) One or more (e.g., one) compounds of this invention;
(b) At least two different antineoplastic agents selected from the group consisting of:
(1) Taxanes;
(2) Platinum coordinator compounds;
(3) Anti-tumor nucleoside derivatives;
(4) Topoisomerase inhibitors; and
(5) Vinca alkaloids.

This invention also provides a method of treating cancer in a patient in need of such treatment, said treatment comprising administering therapeutically effective amounts of:
(a) One or more (e.g., one) compounds of this invention;
(b) Carboplatin; and
(c) Paclitaxel.

This invention also provides a method of treating cancer in a patient in need of such treatment, said treatment comprising administering therapeutically effective amounts of:
(a) One or more (e.g., one) compounds of this invention;
(b) Cisplatin; and
(c) Gemcitabine.

This invention also provides a method of treating cancer in a patient in need of such treatment, said treatment comprising administering therapeutically effective amounts of:
(a) One or more (e.g., one) compounds of this invention;
(b) Carboplatin; and
(c) Gemcitabine.

This invention also provides a method of treating cancer in a patient in need of such treatment, said treatment comprising administering therapeutically effective amounts of:
(a) One or more (e.g., one) compounds of this invention;
(b) Carboplatin; and
(c) Docetaxel.

This invention also provides a method of treating cancer in a patient in need of such treatment, said treatment comprising administering therapeutically effective amounts of:
- (a) One or more (e.g., one) compounds of this invention; and
- (b) An antineoplastic agent selected from the group consisting of:
  - (1) EGF inhibitors that are antibodies;
  - (2) EGF inhibitors that are small molecules;
  - (3) VEGF inhibitors that are antibodies; and
  - (4) VEGF kinase inhibitors that are small molecules.

This invention also provides a method of treating squamous cell cancer of the head and neck, in a patient in need of such treatment, said treatment comprising administering therapeutically effective amounts of:
- (a) One or more (e.g., one) compounds of this invention; and
- (b) One or more antineoplastic agents selected from the group consisting of:
  - (1) Taxanes; and
  - (2) Platinum coordinator compounds.

This invention also provides a method of treating squamous cell cancer of the head and neck, in a patient in need of such treatment, said treatment comprising administering therapeutically effective amounts of:
- (a) One or more (e.g., one) compounds of this invention; and
- (b) At least two different antineoplastic agents selected from the group consisting of:
  - (1) Taxanes;
  - (2) Platinum coordinator compounds; and
  - (3) Anti-tumor nucleoside derivatives (e.g., 5-Fluorouracil).

This invention also provides a method of treating CML in a patient in need of such treatment, said treatment comprising administering therapeutically effective amounts of:
- (a) One or more (e.g., one) compounds of this invention;
- (b) Gleevec; and
- (c) Interferon (e.g., Intron-A).

This invention also provides a method of treating CML in a patient in need of such treatment, said treatment comprising administering therapeutically effective amounts of:
- (a) One or more (e.g., one) compounds of this invention;
- (b) Gleevec; and
- (c) Pegylated interferon (e.g., Peg-Intron, and Pegasys).

This invention also provides a method of treating AML in a patient in need of such treatment, said treatment comprising administering therapeutically effective amounts of:
- (a) One or more (e.g., one) compounds of this invention;
- (b) An anti-tumor nucleoside derivative (e.g., Cytarabine (i.e., Ara-C)).

This invention also provides a method of treating CML in a patient in need of such treatment comprising administering therapeutically effective amounts of: (a) one or more (e.g., one) compounds of this invention and (b) Gleevec.

This invention also provides a method of treating CMML in a patient in need of such treatment comprising administering therapeutically effective amounts of one or more (e.g., one) compounds of this invention.

This invention also provides a method of treating AML in a patient in need of such treatment, said treatment comprising administering therapeutically effective amounts of:
- (a) One or more (e.g., one) compounds of this invention;
- (b) An anti-tumor nucleoside derivative (e.g., Cytarabine (i.e., Ara-C)); and
- (c) An anthracycline.

This invention also provides a method of treating non-Hodgkin's lymphoma in a patient in need of such treatment, said treatment comprising administering therapeutically effective amounts of:
- (a) One or more (e.g., one) compounds of this invention; and
- (b) Rituximab (Rituxan).

This invention also provides a method of treating non-Hodgkin's lymphoma in a patient in need of such treatment, said treatment comprising administering therapeutically effective amounts of:
- (a) One or more (e.g., one) compounds of this invention;
- (b) Rituximab (Rituxan); and
- (c) an anti-tumor nucleoside derivative (e.g., Fludarabine (i.e., F-ara-A).

This invention also provides a method of treating non-Hodgkin's lymphoma in a patient in need of such treatment, said treatment comprising administering therapeutically effective amounts of:
- (a) One or more (e.g., one) compounds of this invention;
- (b) Genasense (antisense to BCL-2).

This invention also provides a method of treating multiple myeloma in a patient in need of such treatment, said treatment comprising administering therapeutically effective amounts of:
- (a) One or more (e.g., one) compounds of this invention; and
- (b) A proteosome inhibitor (e.g., PS-341 (Millenium)).

This invention also provides a method of treating multiple myeloma in a patient in need of such treatment, said treatment comprising administering therapeutically effective amounts of:
- (a) One or more (e.g., one) compounds of this invention; and
- (b) Thalidomide or related imid.

This invention also provides a method of treating multiple myeloma in a patient in need of such treatment, said treatment comprising administering therapeutically effective amounts of:
- (a) One or more (e.g., one) compounds of this invention; and
- (b) Thalidomide.

This invention is also directed to the methods of treating cancer described herein, particularly those described above, wherein in addition to the administration of the compounds of this invention and antineoplastic agents, radiation therapy is also administered prior to, during, or after the treatment cycle.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount (e.g. a therapeutically effective amount) of one or more (e.g., one) compounds of the invention to a patient (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The compounds of this invention useful in the methods of this invention inhibit or treat the abnormal growth of cells. Without wishing to be bound by theory, it is believed that these compounds may function through the inhibition of G-protein function, such as Ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

The method of treating proliferative diseases (cancers, i.e., tumors), according to this invention, includes a method for treating (inhibiting) the abnormal growth of cells, including transformed cells, in a patient in need of such treatment, by administering, concurrently or sequentially, an effective amount of one or more (e.g., one) compounds of this invention and an effective amount of a chemotherapeutic agent and/or radiation.

Other embodiments of the methods of the present invention include methods for treating or inhibiting tumor growth in a patient in need of such treatment by administering, concurrently or sequentially, (1) an effective amount of one or more (e.g., one) compounds of this invention and (2) an effective amount of at least one antineoplastic agent, microtubule affecting agent and/or radiation therapy. For example, one embodiment of these methods is directed to a method of treating cancers selected from the group consisting of: lung cancer, prostate cancer and myeloid leukemias.

The methods of treating proliferative diseases, according to this invention, also include a method for treating (inhibiting) proliferative diseases, both benign and malignant, wherein ras proteins are aberrantly activated as a result of oncogenic mutation in other genes—i.e., the ras gene itself is not activated by mutation to an oncogenic form. This method comprises administering, concurrently or sequentially, an effective amount of a compound of this invention and an effective amount of an antineoplastic agent and/or radiation therapy to a patient in need of such treatment. Examples of such proliferative diseases that may be treated include: the benign proliferative disorder neurofibromatosis, or tumors in which ras is activated due to mutation or overexpression of tyrosine kinase oncogenes (e.g., neu, src, abl, lck, lyn, fyn).

For radiation therapy, γ-radiation is preferred.

The methods of treating proliferative diseases (cancers, i.e., tumors), according to this invention, also include a method for treating (inhibiting) the abnormal growth of cells, including transformed cells, in a patient in need of such treatment, by administering, concurrently or sequentially, an effective amount of a compound of this invention and an effective amount of at least one signal transduction inhibitor.

Typical signal transduction inhibitors include but are not limited to:

(i) Bcr/abl kinase inhibitors such as, for example, STI 571 (Gleevec);

(ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin® (trastuzumab).

Embodiments of the methods of treatment of this invention are directed to the use of a combination of drugs (compounds) for the treatment of cancer, i.e., this invention is directed to a combination therapy for the treatment of cancer. Those skilled in the art will appreciate that the drugs are generally administered individually as a pharmaceutical composition. The use of a pharmaceutical composition comprising more than one drug is within the scope of this invention.

The antineoplastic agents are usually administered in the dosage forms that are readily available to the skilled clinician, and are generally administered in their normally prescribed amounts (as for example, the amounts described in the Physician's Desk Reference, 57$^{th}$ Edition, 2003 (published by Thompson PDR, Montvale, N.J. 07645-1742 the disclosure of which is incorporated herein by reference thereto), or the amounts described in the manufacture's literature for the use of the agent).

For example, the compounds of formula 1.0 can be administered orally (e.g., as a capsule), and the antineoplastic agents can be administered intravenously, usually as an IV solution. The use of a pharmaceutical composition comprising more than one drug is within the scope of this invention.

The compounds of formula 1.0 and the antineoplastic agents are administered in therapeutically effective dosages to obtain clinically acceptable results, e.g., reduction or elimination of symptoms or of the tumor. Thus, the compounds of formula 1.0 and antineoplastic agents can be administered concurrently or consecutively in a treatment protocol. The administration of the antineoplastic agents can be made according to treatment protocols already known in the art.

The compounds of formula 1.0 and antineoplastic agents are administered in a treatment protocol that usually lasts one to seven weeks, and is repeated typically from 6 to 12 times. Generally the treatment protocol lasts one to four weeks. Treatment protocols of one to three weeks may also be used. A treatment protocol of one to two weeks may also be used. During this treatment protocol or cycle the FPT inhibitor is administered daily while the antineoplastic agents are administered one or more times a week. Generally, the compounds of formula 1.0 can be administered daily (i.e., once per day), preferably twice per day, and the antineoplastic agent is administered once a week or once every three weeks. For example, the taxanes (e.g., Paclitaxel (e.g., Taxol®) or Docetaxel (e.g., Taxotere®)) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the compounds of formula 1.0 can be administered discontinuously rather than continuously during the treatment cycle. Thus, for example, during the treatment cycle the compounds of formula 1.0 can be administered daily for a week and then discontinued for a week, with this administration repeating during the treatment cycle. Or the compounds of formula 1.0 can be administered daily for two weeks and discontinued for a week, with this administration repeating during the treatment cycle. Thus, the compounds of formula 1.0 can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the compounds of formula 1.0 are not dosed does not have to equal the number of days (or weeks) wherein the compounds of formula 1.0 are dosed. Usually, if a discontinuous dosing protocol is used, the number of days or weeks that the compounds of formula 1.0 are dosed are at least equal or greater than the number of days or weeks that the compounds of formula 1.0 are not dosed.

The antineoplastic agent could be given by bolus or continuous infusion. The antineoplastic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

The compounds of formula 1.0 can be administered orally, preferably as a solid dosage form, more preferably a capsule, and while the total therapeutically effective daily dose can be administered in one to four, or one to two divided doses per day, generally, the therapeutically effective dose is given once or twice a day, preferably twice a day. Examples of dosages for the compounds of formula 1.0 include but are not limited to: about 50 to about 400 mg once per day, about 50 to about 300 mg once per day, about 50 to about 350 mg twice a day, about 50 mg to about 200 mg twice a day, about 75 mg to about 125 mg administered twice a day, or about 100 mg administered twice a day.

If the patient is responding, or is stable, after completion of the therapy cycle, the therapy cycle can be repeated according to the judgment of the skilled clinician. Upon completion of the therapy cycles, the patient can be continued on the compounds of formula 1.0 at the same dose that was administered in the treatment protocol, or, if the dose was less than 200 mg twice a day, the dose can be raised to 200 mg twice a day. This maintenance dose can be continued until the patient progresses or can no longer tolerate the dose (in which case the dose can be reduced and the patient can be continued on the reduced dose).

The antineoplastic agents used with the compounds of formula 1.0 are administered in their normally prescribed dosages during the treatment cycle (i.e., the antineoplastic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (f) about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25 mg/m$^2$/day every 3 to 4 weeks; (l) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (o) about 1 to about 350 mg/m$^2$ for topoisomerase inhibitors; (p) about 1 to about 50 mg/m$^2$ for vinca alkaloids; (q) for the folate antagonist Methotrexate (MTX) 20-60 mg/m$^2$ by oral, IV or IM every 3 to 4 weeks, the intermediate dose regimen is 80-250 mg/m$^2$ IV over 60 minutes every 3 to 4 weeks, and the high dose regimen is 250-1000 mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); and (z) for the biologic Rituximab (Rituxan) (antibody used for non-Hodgkin's lymphoma) 200-400 mg/m$^2$ IV weekly over 4-8 weeks for 6 months.

Gleevec can be used orally in an amount of about 200 to about 800 mg/day.

Thalidomide (and related imids) can be used orally in amounts of about 200 to about 800 mg/day, and can be continuously dosed or used until relapse or toxicity. See for example Mitsiades et al., "Apoptotic signaling induced by immunomodulatory thalidomide analogs in human multiple myeloma cells; therapeutic implications", Blood, 99(12):4525-30, Jun. 15, 2002, the disclosure of which is incorporated herein by reference thereto.

For example, Paclitaxel (e.g., Taxol® can be administered once per week in an amount of about 50 to about 100 mg/m$^2$ with about 60 to about 80 mg/m$^2$ being preferred. In another example Paclitaxel (e.g., Taxol® can be administered once every three weeks in an amount of about 150 to about 250 mg/m$^2$ with about 175 to about 225 mg/m$^2$ being preferred.

In another example, Docetaxel (e.g., Taxotere®) can be administered once per week in an amount of about 10 to about 45mg/m$^2$. In another example Docetaxel (e.g., Taxotere®) can be administered once every three weeks in an amount of about 50 to about 100 mg/m$^2$.

In another example Cisplatin can be administered once per week in an amount of about 20 to about 40 mg/m$^2$. In another example Cisplatin can be administered once every three weeks in an amount of about 60 to about 100 mg/m$^2$.

In another example Carboplatin can be administered once per week in an amount to provide an AUC of about 2 to about 3. In another example Carboplatin can be administered once every three weeks in an amount to provide an AUC of about 5 to about 8.

Antineoplastic agents that can be used in combination with the compounds of formula 1.0 are:

(1) Taxanes such as paclitaxel (TAXOL®) and/or docetaxel (Taxotere®);

(2) Platinum coordinator compounds, such as, for example, carboplatin, cisplatin and oxaliplatin;

(3) EGF inhibitors that are antibodies, such as: HER2 antibodies (such as, for example trastuzumab (Herceptin®, Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithkline), CI 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);

(4) EGF inhibitors that are small molecules, such as, Tarceva (TM) (OSI-774, OSI Pharmaceuticals, Inc.), and Iressa (ZD 1839, Astra Zeneca);

(5) VEGF inhibitors that are antibodies such as: bevacizumab (Genentech, Inc.), and IMC-1C11 (ImClone Systems), DC 101 (a KDR VEGF Receptor 2 from ImClone Systems);

(6) VEGF kinase inhibitors that are small molecules such as SU 5416 and SU 6688 (both from Sugen, Inc.);

(7) Estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.);

(8) Anti-tumor nucleoside derivatives such as 5-fluorouracil, gemcitabine or capecitabine;

(9) Epothilones such as BMS-247550 (Bristol-Myers Squibb), and EPO906 (Novartis Pharmaceuticals);

(10) Topoisomerase inhibitors such as topotecan (Glaxo SmithKline), and Camptosar (Pharmacia);

(11) Vinca alkaloids, such as, navelbine (Anvar and Fabre, France), vincristine and vinblastine; and

(12) Antibodies that are inhibitors of αVβ3 integrins, such as, LM-609 (see, Clinical Cancer Research, Vol. 6, page 3056-3061, August 2000, the disclosure of which is incorporated herein by reference thereto).

In one embodiment the antineoplastic agents are selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 or SU6688.

In another embodiment the antineoplastic agents are selected from: paclitaxel, docetaxel, carboplatin, cisplatin, navelbine, gemcitabine, or Herceptin.

In general when more than one antineoplastic agent is used in the methods of this invention, the antineoplastic agents are administered on the same day either concurrently or consecutively in their standard dosage form. For example, the antineoplastic agents are usually administered intravenously, preferably by an IV drip using IV solutions well known in the art (e.g., isotonic saline (0.9% NaCl) or dextrose solution (e.g., 5% dextrose)).

When two or more antineoplastic agents are used, the antineoplastic agents are generally administered on the same day; however, those skilled in the art will appreciate that the antineoplastic agents can be administered on different days and in different weeks. The skilled clinician can administer the antineoplastic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

Thus, one embodiment of this invention is directed to a method of treating cancer, said treatment comprising administering to a patient in need of such treatment therapeutically effective amounts of one or more (e.g., one) compounds of formula 1.0, a taxane, and a platinum coordination compound.

Another embodiment of this invention is directed to a method of treating cancer comprising administering to a patient in need of such treatment therapeutically effective amounts of one or more (e.g., one) compounds of formula 1.0, a taxane, and a platinum coordination compound, wherein said compound of formula 1.0 is administered every day, said taxane is administered once per week per cycle, and said platinum coordinator compound is administered once per week per cycle. In one embodiment, the treatment is for one to four weeks per cycle.

Another embodiment of this invention is directed to a method of treating cancer comprising administering to a patient in need of such treatment therapeutically effective amounts of one or more (e.g., one) compounds of formula 1.0, a taxane, and a platinum coordination compound, wherein said compound of formula 1.0 is administered every day, said taxane is administered once every three weeks per cycle, and said platinum coordinator compound is administered once every three weeks per cycle. in one embodiment, the treatment is for one to three weeks per cycle.

Another embodiment of this invention is directed to a method of treating cancer, said treatment comprising administering to a patient in need of such treatment therapeutically effective amounts of one or more (e.g., one) compounds of formula 1.0, paclitaxel, and carboplatin. In one embodiment, said FPT inhibitor is administered every day, said paclitaxel is administered once per week per cycle, and said carboplatin is administered once per week per cycle. In another embodiment, the treatment is for one to four weeks per cycle.

Another embodiment of this invention is directed to a method of treating cancer, said treatment comprising administering to a patient in need of such treatment therapeutically effective amounts of one or more (e.g., one) compounds of formula 1.0, paclitaxel, and carboplatin. In one embodiment, said compound of formula 1.0 is administered every day, said paclitaxel is administered once every three weeks per cycle, and said carboplatin is administered once every three weeks per cycle. In another embodiment, the treatment is for one to three weeks per cycle.

Other embodiments of this invention are directed to methods of treating cancer as described in the above embodiments except that in place of paclitaxel and carboplatin the taxanes and platinum coordinator compounds used together in the methods are: (1) docetaxel (Taxotere®) and cisplatin; (2) paclitaxel and cisplatin; and (3) docetaxel and carboplatin. In one embodiment of the methods of this invention the cisplatin is used in amounts of about 30 to about 100 mg/m$^2$. In one embodiment of the methods of this invention docetaxel is used in amounts of about 30 to about 100 mg/m$^2$.

In another embodiment this invention is directed to a method of treating cancer, said treatment comprising administering to a patient in need of such treatment therapeutically effective amounts of one or more (e.g., one) compounds of formula 1.0, a taxane, and an EGF inhibitor that is an antibody. In one embodiment the taxane used is paclitaxel, and the EGF inhibitor is a HER2 antibody (e.g., Herceptin) or Cetuximab, and in one embodiment Herceptin is used. The length of treatment, and the amounts and administration of the compounds of formula 1.0 and the taxane are as described in the embodiments above. The EGF inhibitor that is an antibody is administered once a week per cycle, and, in one embodiment, is administered on the same day as the taxane, and in another embodiment is administered consecutively with the taxane. For example, Herceptin is administered in a loading dose of about 3 to about 5 mg/m$^2$ (preferably about 4 mg/m$^2$), and then is administered in a maintenance dose of about 2 mg/m$^2$ once per week per cycle for the remainder of the treatment cycle (usually the cycle is 1 to 4 weeks). In one embodiment, the cancer treated is breast cancer.

In another embodiment this invention is directed to a method of treating cancer, said treatment comprising administering to a patient in need of such treatment therapeutically effective amounts of:

(1) One or more (e.g., one) compounds of formula 1.0;
(2) A taxane; and
(3) An antineoplastic agent selected from the group consisting of:
 (a) An EGF inhibitor that is a small molecule;
 (b) A VEGF inhibitor that is an antibody; and
 (c) A VEGF kinase inhibitor that is a small molecule.

In one embodiment, the taxane paclitaxel or docetaxel is used. In another embodiment, the antineoplastic agent is selected from: tarceva, Iressa, bevacizumab, SU5416 or SU6688. The length of treatment, and the amounts and administration of the compound of formula 1.0 and the taxane are as described in the embodiments above. The VEGF kinase inhibitor that is an antibody is usually given once per week per cycle. The EGF and VEGF inhibitors that are small molecules are usually given daily per cycle. In one embodiment, the VEGF inhibitor that is an antibody is given on the same day as the taxane, and in another embodiment is administered concurrently with the taxane. When the EGF inhibitor that is a small molecule or the VEGF inhibitor that is a small molecule is administered on the same day as the taxane, the administration, in one embodiment, is concurrently with the taxane. The EGF or VEGF kinase inhibitor is generally administered in an amount of about 10 to about 500 mg/m$^2$.

In another embodiment this invention is directed to a method of treating cancer, said treatment comprising administering to a patient in need of such treatment therapeutically effective amounts of one or more (e.g., one) compounds of this invention, an anti-tumor nucleoside derivative, and a platinum coordination compound.

Another embodiment of this invention is directed to a method of treating cancer, said treatment comprising administering to a patient in need of such treatment therapeutically effective amounts of one or more (e.g., one) compounds of this invention, an anti-tumor nucleoside derivative, and a platinum coordination compound, wherein said compounds of the invention are administered every day, said anti-tumor nucleoside derivative is administered once per week per cycle, and said platinum coordinator compound is administered once per week per cycle. Although the treatment can be for one to four weeks per cycle, the treatment, in one embodiment, is for one to seven weeks per cycle.

Another embodiment of this invention is directed to a method of treating cancer, said treatment comprising administering to a patient in need of such treatment therapeutically effective amounts of one or more (e.g., one) compounds of this invention, an anti-tumor nucleoside derivative, and a platinum coordination compound, wherein said compounds of this invention are administered every day, said an anti-tumor nucleoside derivative is administered once per week per cycle, and said platinum coordinator compound is administered once every three weeks per cycle. Although the treatment can be for one to four weeks per cycle, the treatment in one embodiment, is for one to seven weeks per cycle.

Another embodiment of this invention is directed to a method of treating cancer, said treatment comprising administering to a patient in need of such treatment therapeutically effective amounts of one or more (e.g., one) compounds of this invention, gemcitabine, and cisplatin. In one embodiment, said compounds of this invention are administered every day, said gemcitabine is administered once per week per cycle, and said cisplatin is administered once per week per cycle. In one embodiment, the treatment is for one to seven weeks per cycle.

Another embodiment of this invention is directed to a method of treating cancer, said treatment comprising administering to a patient in need of such treatment therapeutically effective amounts of one or more (e.g., one) compounds of this invention, gemcitabine, and cisplatin. In one embodiment, said compounds of this invention are administered every day, said gemcitabine is administered once per week per cycle, and said cisplatin is administered once every three weeks per cycle. In one embodiment, the treatment is for one to seven weeks.

Another embodiment of this invention is directed to a method of treating cancer, said treatment comprising administering to a patient in need of such treatment therapeutically effective amounts of one or more (e.g., one) compounds of this invention), gemcitabine, and carboplatin. In one embodiment, said compounds of this invention are administered every day, said gemcitabine is administered once per week per cycle, and said carboplatin is administered once per week per cycle. In another embodiment, the treatment is for one to seven weeks per cycle.

Another embodiment of this invention is directed to a method of treating cancer, said treatment comprising administering to a patient in need of such treatment therapeutically effective amounts of one or more (e.g., one) compounds of this invention, gemcitabine, and carboplatin. In one embodiment, said compounds of the invention are administered every day, said gemcitabine is administered once per week per cycle, and said carboplatin is administered once every three weeks per cycle. In one embodiment, the treatment is for one to seven weeks per cycle.

In the above embodiments using gemcitabine, the compounds of this invention and the platinum coordinator compound are administered as described above for the embodiments using taxanes. Gemcitabine is administered in an amount of about 500 to about 1250 mg/m$^2$. The gemcitabine, in one embodiment, is administered on the same day as the platinum coordinator compound, and in another embodiment consecutively with the platinum coordinator compound, and in another embodiment gemcitabine is administered after the platinum coordinator compound.

Another embodiment of this invention is directed to a method of treating cancer in a patient in need of such treatment comprising administering to said patient one or more (e.g., one) compounds of this invention and an antineoplastic agent selected from: (1) EGF inhibitors that are antibodies, (2) EGF inhibitors that are small molecules, (3) VEGF inhibitors that are antibodies, and (4) VEGF kinase inhibitors that are small molecules all as described above. The treatment is for one to seven weeks per cycle, and generally for one to four weeks per cycle. The compounds of this invention are administered in the same manner as described above for the other embodiments of this invention. The small molecule antineoplastic agents are usually administered daily, and the antibody antineoplastic agents are usually administered once per week per cycle. The antineoplastic agents, in one embodiment, are selected from: Herceptin, Cetuximab, Tarceva, Iressa, bevacizumab, IMC-1C11, SU5416 or SU6688.

Other embodiments of this invention are directed to the use of a combination of at least one (e.g., one) compound of formula 1.0 and drugs for the treatment of breast cancer, i.e., this invention is directed to a combination therapy for the treatment of breast cancer. Those skilled in the art will appreciate that the compounds of formula 1.0 and drugs are generally administered as individual pharmaceutical compositions. The use of a pharmaceutical composition comprising more than one drug is within the scope of this invention.

Thus, another embodiment of this invention is directed to a method of treating (or preventing) breast cancer (i.e., postmenopausal and premenopausal breast cancer, e.g., hormonedependent breast cancer) in a patient in need of such treatment comprising administering to said patient a therapeutically effective amount of at least one (e.g., one) compound of formula 1.0 and a therapeutically effective amount of at least one antihormonal agent selected from the group consisting of:
(a) aromatase inhibitors;
(b) antiestrogens; and
(c) LHRH analogues; and said treatment optionally including the administration of at least one chemotherapeutic agent.

The compounds of formula 1.0, in one embodiment, are administered orally, and, in another embodiment, are administered in capsule form.

Examples of aromatase inhibitors include but are not limited to: Anastrozole (e.g., Arimidex), Letrozole (e.g., Femara), Exemestane (Aromasin), Fadrozole and Formestane (e.g., Lentaron).

Examples of antiestrogens include but are not limited to: Tamoxifen (e.g., Nolvadex), Fulvestrant (e.g., Faslodex), Raloxifene (e.g., Evista), and Acolbifene.

Examples of LHRH analogues include but are not limited to: Goserelin (e.g., Zoladex) and Leuprolide (e.g., Leuprolide Acetate, such as Lupron or Lupron Depot).

Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

Preferably, when more than one antihormonal agent is used, each agent is selected from a different category of agent. For example, one agent is an aromatase inhibitor (e.g., Anastrozole, Letrozole, or Exemestane) and one agent is an antiestrogen (e.g., Tamoxifen or Fulvestrant).

Another embodiment of this invention is directed to a method of treating or preventing breast cancer in a patient in need of such treatment wherein said treatment comprises administering a therapeutically effective amount of at least one (e.g., one) compound of formula 1.0 and at least one antihormonal agent selected from the group consisting of:
(a) aromatase inhibitors;
(b) antiestrogens; and
(c) LHRH analogues; and administering an effective amount of at least one chemotherapeutic agent.

Another embodiment of this invention is directed to a method of treating or preventing breast cancer in a patient in need of such treatment wherein said treatment comprises administering a therapeutically effective amount of at least one compound of formula 1.0 (e.g., one) and at least one antihormonal agent selected from the group consisting of:
(a) aromatase inhibitors;
(b) antiestrogens; and
(c) LHRH analogues.

Another embodiment of this invention is directed to a method of treating or preventing breast cancer in a patient in need of such treatment wherein said treatment comprises administering a therapeutically effective amount of at least one compound of formula 1.0 (e.g., one) and at least one antihormonal agent selected from the group consisting of:
(a) aromatase inhibitors; and
(b) antiestrogens.

Another embodiment of this invention is directed to a method of treating or preventing breast cancer in a patient in need of such treatment wherein said treatment comprises administering a therapeutically effective amount of at least one compound of formula 1.0 (e.g., one), at least one antihormonal agent selected from the group consisting of:
(a) aromatase inhibitors; and
(b) antiestrogens; and at least one chemotherapeutic agent.

Another embodiment of this invention is directed to a method of treating or preventing breast cancer in a patient in need of such treatment wherein said treatment comprises administering a therapeutically effective amount of at least one compound of formula 1.0 (e.g., one) and at least one aromatase inhibitor.

Another embodiment of this invention is directed to a method of treating or preventing breast cancer in a patient in need of such treatment wherein said treatment comprises administering a therapeutically effective amount of at least one compound of formula 1.0 (e.g., one), at least one aromatase inhibitor, and at least one chemotherapeutic agent.

Another embodiment of this invention is directed to a method of treating or preventing breast cancer in a patient in need of such treatment wherein said treatment comprises administering a therapeutically effective amount of:
at least one compound of formula 1.0 (e.g., one);
at least one antihormonal agent selected from the group consisting of:
(a) aromatase inhibitors that are selected from the group consisting of Anastrozole, Letrozole, Exemestane, Fadrozole and Formestane;
(b) antiestrogens that are selected from the group consisting of: Tamoxifen, Fulvestrant, Raloxifene, and Acolbifene; and
(c) LHRH analogues that are selected from the group consisting of: Goserelin and Leuprolide; and administering an effective amount of at least one chemotherapeutic agents are selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of:
at least one compound of formula 1.0 (e.g., one);
at least one antihormonal agent selected from the group consisting of:
(a) aromatase inhibitors that are selected from the group consisting of Anastrozole, Letrozole, Exemestane, Fadrozole and Formestane;
(b) antiestrogens that are selected from the group consisting of: Tamoxifen, Fulvestrant, Raloxifene, and Acolbifene; and
(c) LHRH analogues that are selected from the group consisting of: Goserelin and Leuprolide.

Another embodiment of this invention is directed to a method of treating or preventing breast cancer in a patient in need of such treatment wherein said treatment comprises administering a therapeutically effective amount of:
at least one compound of formula 1.0 (e.g., one);
at least one antihormonal agent selected from the group consisting of:
(a) aromatase inhibitors that are selected from the group consisting of Anastrozole, Letrozole, Exemestane, Fadrozole and Formestane; and
(b) antiestrogens that are selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of:

at least one compound of formula 1.0 (e.g., one);
at least one antihormonal agent selected from the group consisting of:
(a) aromatase inhibitors that are selected from the group consisting of Anastrozole, Letrozole, Exemestane, Fadrozole and Formestane;
(b) antiestrogens that are selected from the group consisting of: Tamoxifen, Fulvestrant, Raloxifene, and Acolbifene; and administering an effective amount of at least one chemotherapeutic agents are selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of:

at least one compound of formula 1.0 (e.g., one); and
at least one aromatase inhibitor selected from the group consisting of Anastrozole, Letrozole, Exemestane, Fadrozole and Formestane.

Another embodiment of this invention is directed to a method of treating or preventing breast cancer in a patient in need of such treatment wherein said treatment comprises administering a therapeutically effective amount of:

at least one compound of formula 1.0 (e.g., one);
at least one aromatase inhibitor that is selected from the group consisting of Anastrozole, Letrozole, Exemestane, Fadrozole and Formestane; and
administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of:

(a) at least one compound of formula 1.0 (e.g., one);
(b) at least one aromatase inhibitor; and
(c) at least one LHRH analogue.

Another embodiment of this invention is directed to a method of treating or preventing breast cancer in a patient in need of such treatment wherein said treatment comprises administering a therapeutically effective amount of:

(a) at least one compound of formula 1.0 (e.g., one);
(b) at least one antiestrogen; and
(c) at least one LHRH analogue.

Another embodiment of this invention is directed to a method of treating or preventing breast cancer in a patient in need of such treatment wherein said treatment comprises administering a therapeutically effective amount of:

(a) at least one compound of formula 1.0 (e.g., one);
(b) at least one aromatase inhibitor that is selected from the group consisting of Anastrozole, Letrozole, Exemestane, Fadrozole and Formestane; and
(c) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of:

(a) at least one compound of formula 1.0 (e.g., one);
(b) at least one antiestrogen that is selected from the group consisting of: Tamoxifen, Fulvestrant, Raloxifene, and Acolbifene; and
(c) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of at least one compound of formula 1.0 (e.g., one) and Anastrozole.

Another embodiment of this invention is directed to a method of treating or preventing breast cancer in a patient in need of such treatment wherein said treatment comprises administering a therapeutically effective amount of at least one compound of formula 1.0 (e.g., one) and Letrazole.

Another embodiment of this invention is directed to a method of treating or preventing breast cancer in a patient in need of such treatment wherein said treatment comprises administering a therapeutically effective amount of at least one compound of formula 1.0 (e.g., one) and Exemestane.

Another embodiment of this invention is directed to a method of treating or preventing breast cancer in a patient in need of such treatment wherein said treatment comprises administering a therapeutically effective amount of at least one compound of formula 1.0 (e.g., one) and Fadrozole.

Another embodiment of this invention is directed to a method of treating or preventing breast cancer in a patient in need of such treatment wherein said treatment comprises administering a therapeutically effective amount of at least one compound of formula 1.0 (e.g., one) and Formestane.

Another embodiment of this invention is directed to a method of treating or preventing breast cancer in a patient in need of such treatment wherein said treatment comprises administering a therapeutically effective amount of at least one compound of formula 1.0 (e.g., one) and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one) Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one) and Raloxifene.

Another embodiment of this invention is directed to a method of treating or preventing breast cancer in a patient in need of such treatment wherein said treatment comprises administering a therapeutically effective amount of at least one compound of formula 1.0 (e.g., one) and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one) and Goserelin.

Another embodiment of this invention is directed to a method of treating or preventing breast cancer in a patient in need of such treatment wherein said treatment comprises administering a therapeutically effective amount of at least one compound of formula 1.0 (e.g., one) and Leuprolide.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Formestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Formestane, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Formestane, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Formestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Raloxifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Goserelin, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Leuprolein, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula. 1.0 (e.g., one), Anastrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Formestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Formestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Anastrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Letrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Exemestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Fadrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Formestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Goserelin, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Goserelin, and Raloxifene.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide, and Tamoxifen.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide, and Fulvestrant.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide, and Raloxifene.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Acolbifene.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Anastrozole.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Letrozole.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Exemestane.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Fadrozole.

Another embodiment of this invention is directed to a method of treating or preventing breast cancer in a patient in need of such treatment wherein said treatment comprises administering a therapeutically effective amount of at least one compound of formula 1.0 (e.g., one), Goserelin and Formestane.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Anastrozole.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Letrozole.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Exemestane.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Fadrozole.

Another embodiment of this invention is directed to a method of treating or preventing breast cancer in a patient in need of such treatment wherein said treatment comprises administering a therapeutically effective amount of at least one compound of formula 1.0 (e.g., one), Leuprolide and Formestane.

A preferred embodiment of this invention is directed to the treatment or prevention of breast cancer in a patient in need of such treatment, said treatment comprising the administration of a therapeutically effective amount of at least one compound of formula 1.0 (e.g., one) and Anastrozole.

Another preferred embodiment of this invention is directed to the treatment or prevention of breast cancer in a patient in need of such treatment, said treatment comprising the administration of a therapeutically effective amount of at least one compound of formula 1.0 (e.g., one) and Letrozole.

Another preferred embodiment of this invention is directed to the treatment or prevention of breast cancer in a patient in need of such treatment, said treatment comprising the administration of a therapeutically effective amount of at least one compound of formula 1.0 (e.g., one) and Exemestane.

Another preferred embodiment of this invention is directed to the treatment or prevention of breast cancer in a patient in need of such treatment, said treatment comprising the administration of a therapeutically effective amount of at least one compound of formula 1.0 (e.g., one) and Tamoxifen.

Another preferred embodiment of this invention is directed to the treatment or prevention of breast cancer in a patient in need of such treatment, said treatment comprising the administration of a therapeutically effective amount of at least one compound of formula 1.0 (e.g., one) and Fulvestrant.

Another preferred embodiment of this invention is directed to the treatment or prevention of breast cancer in a patient in need of such treatment, said treatment comprising the administration of a therapeutically effective amount of at least one compound of formula 1.0 (e.g., one), Anastrozole, and Fulvestrant.

Another embodiment of this invention is directed to the treatment or prevention of breast cancer in a patient in need of such treatment, said treatment comprising the administration of a therapeutically effective amount of at least one compound of formula 1.0 (e.g., one), Letrozole, and Fulvestrant.

Another embodiment of this invention is directed to the treatment or prevention of breast cancer in a patient in need of such treatment, said treatment comprising the administration of a therapeutically effective amount of at least one compound of formula 1.0 (e.g., one), Exemestane, and Fulvestrant.

Another embodiment of this invention is directed to the treatment or prevention of breast cancer in a patient in need of such treatment, said treatment comprising the administration of a therapeutically effective amount of at least one compound of formula 1.0 (e.g., one), Anastrozole, and Tamoxifen.

Another embodiment of this invention is directed to the treatment or prevention of breast cancer in a patient in need of such treatment, said treatment comprising the administration of a therapeutically effective amount of at least one compound of formula 1.0 (e.g., one), Letrozole, and Tamoxifen.

Another embodiment of this invention is directed to the treatment or prevention of breast cancer in a patient in need of such treatment, said treatment comprising the administration of a therapeutically effective amount of at least one compound of formula 1.0 (e.g., one), Exemestane, and Tamoxifen.

Other embodiments of this invention are directed to any of the above described embodiments for the treatment of Breast Cancer wherein the chemotherapeutic agent is Trastuzumab.

Other embodiments of this invention are directed to any of the above described embodiments for the treatment of Breast Cancer wherein the method is directed to a method of treating breast cancer.

The compounds of formula 1.0, antihormonal agents and chemotherapeutic agents can be administered concurrently or sequentially.

The antihormonal agents and optional chemotherapeutic agents are administered according to their protocols, dosage amounts, and dosage forms that are well know to those skilled in the art (e.g., the Physician's Desk Reference or published literature). For example, for Tamoxifen, Fulvestrant, Raloxifene, Anastrozole, Letrozole, Exemestane, Leuprolide and Goserelin, see the Physician's Desk Reference, $57^{th}$ Edition, 2003, published by Thomas PDR at Montvale, N.J. 07645-1742, the disclosure of which is incorporated herein by reference thereto.

In general, in the embodiments directed to the methods of treating Breast Cancer:

the compounds of formula 1.0 can be administered daily (e.g., once per day, and preferably twice a day), the aromatase inhibitors can be administered in accordance with the known protocol for the aromatase inhibitor used (e.g., once per day), the antiestrogens can be administered in accordance with the known protocol for the antiestrogen used (e.g., from once a day to once a month), the LHRH analogue can be administered in accordance with the known protocol for the LHRH analogue used (e.g., once a month to once every three months), and the chemotherapeutic agent can be administered in accordance with the known protocol for the chemotherapeutic agent used (e.g., from once a day to once a week).

Radiation therapy, if administered, is generally administered according to known protocols before administration of the compounds of formula 1.0, antihormonal agents and optional chemotherapeutic agents.

Treatment according to the methods of treating Breast Cancer is continuous (i.e., a continuous dosing schedule is followed). The treatment is continued until there is a complete response, or until the skilled clinician determines that the patient is not benefiting from the treatment (for example, when there is disease progression).

The continuous treatment protocol for Breast Cancer can be changed to a discontinuous treatment schedule if, in the judgment of the skilled clinician, the patient would benefit from a discontinuous treatment schedule with one or more of the administered drugs. For example, the compounds of formula 1.0 can be given using a discontinuous treatment schedule while the remaining drugs used in the treatment are given as described herein. An example of a discontinuous treatment protocol for the compounds of formula 1.0 is a repeating cycle of three weeks with the compounds of formula 1.0 followed by one week without the compounds of formula 1.0.

After a complete response is achieved with the Breast Cancer treatment, maintenance therapy with the compounds of formula 1.0 can be continued using the dosing described in the methods of this invention. Maintenance therapy can also include administration of the antihormonal agents using the dosing described in the methods of this invention. Maintenance therapy can just be with the antihormonal agents. For example, after a complete response is achieved, an aromatase inhibitor (e.g., Anastrozole, Letrozole or Exemestane) can be continued for up to five years. Or, for example, an antiestrogen, e.g., Tamoxifen, may be used for up to five years after a complete response is achieved. Or, for example, an antiestrogen (e.g., Tamoxifen) can be used for up to five years after a complete response is achieved followed by the use of an aromatase inhibitor (e.g., Anastrozole, Letrozole or Exemestane) for up to five years.

In the embodiments directed to the treatment of Breast Cancer described above, the compounds of formula 1.0 are administered continuously in a total daily dose of about 100 mg to about 600 mg. Usually this amount is administered in divided doses, and in one embodiment twice a day. In one embodiment the compounds of formula 1.0 are dosed twice a day in an amount of about 50 mg to about 300 mg per dose. In another embodiment, the compounds of formula 1.0 are dosed twice a day in an amount of about 100 mg to about 200 mg per dose. Examples include the compounds of formula 1.0 being dosed twice a day at 100 mg per dose. Examples also include the compounds of formula 1.0 being dosed twice a day at 200 mg per dose.

Anastrozole is administered p.o. and is dosed once a day in amounts of about 0.5 to about 10 mg per dose, and in one embodiment in an amount of about 1.0 mg per dose.

Letrozole is administered p.o. and is dosed once a day in amounts of about 1.0 to about 10 mg per dose, and in one embodiment in an amount of about 2.5 mg per dose.

Exemestane is administered p.o. and is dosed once a day in amounts of about 10 to about 50 mg per dose, and in one embodiment in an amount of about 25 mg per dose.

Fadrozole is administered p.o. and is dosed twice a day in amounts of about 0.5 to about 10 mg per dose, and in one embodiment in an amount of about 2.0 mg per dose.

Formestane is administered i.m. and is dosed once every two weeks in amounts of about 100 to about 500 mg per dose, and in one embodiment in an amount of about 250 mg per dose.

Tamoxifen is administered p.o. and is dosed once a day in amounts of about 10 to about 100 mg per dose, and in one embodiment in an amount of about 20 mg per dose.

Fulvestrant is administered i.m. and is dosed once a month in amounts of about 100 to about 1000 mg per dose, and in one embodiment in an amount of about 250 mg per dose.

Raloxifene is administered p.o. and is dosed once a day in amounts of about 10 to about 120 mg per dose, and in one embodiment in an amount of about 60 mg per dose.

Acolbifene is administered p.o. and is dosed once a day in amounts of about 5 to about 20 mg per dose, and in one embodiment in an amount of about 20 mg per dose.

Goserelin is administered s.c. and is dosed once a month, or once every three months, in amounts of about 2 to about 20 mg per dose, and in one embodiment in an amount of about 3.6 mg per dose when administered once a month, and in another embodiment in an amount of about 10.8 mg per dose when administered once every three months.

Leuprolide is administered s.c. and is dosed once a month, or once every three months, in amounts of about 2 to about 20 mg per dose, and in one embodiment in an amount of about 3.75 mg per dose when administered once a month, and in another embodiment in an amount of about 11.25 mg per dose when administered once every three months.

Trastuzumab is administered by i.v. and is dosed once a week in amounts of about 2 to about 20 mpk per dose, and in one embodiment in an amount of about 2 mpk per dose. Trastuzumab is generally initially administered in a loading dose that is generally twice the dose of the weekly dose. Thus, for example, a 4 mpk loading dose is administered and then dosing is 2 mpk per dose per week.

Gefitinib is administered p.o. and is dosed once a day in amounts of about 100 to about 1000 mg per dose, and in one embodiment in an amount of about 250 mg per dose.

Erlotinib is administered p.o. and is dosed once a day in amounts of about 100 to about 500 mg per dose, and in one embodiment in an amount of about 150 mg per dose.

Bevacizumab is administered i.v. and is dosed once every two weeks in amounts of about 2.5 to about 15 mg per kilogram of body weight per dose, and in one embodiment in an amount of about 10 mg per kilogram per dose.

Cetuximab is administered i.v. and is dosed once a week in amounts of about 200 to about 500 mg per meter squared dose, and in one embodiment in an amount of about 250 mg per meter squared per dose.

Bortezomib is administered i.v. and is dosed twice a week for 2 weeks followed by a 10 day rest period (21 day treatment cycle) for a maximum of 8 treatment cycles in amounts of about 1.0 to about 2.5 mg per meter squared per dose, and in one embodiment in an amount of about 1.3 mg per meter squared per dose.

Thus in one embodiment of this invention breast cancer is treated (or prevented) in a patient in need of such treatment wherein said treatment comprises administering to said patient: (a) at least one compound of formula 1.0 (usually one) orally in an amount of about 50 mg to about 300 mg per dose wherein each dose is administered twice a day, and (b) Anastrozole p.o. in an amount of about 0.5 to about 10 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) orally in an amount of about 100 to 200 mg per dose, wherein each dose is administered twice a day, and (b) Anastrozole in an amount of about 1.0 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) orally in an amount of about 50 mg to about 300 mg per dose wherein each dose is administered twice a day, and (b) Letrozole p.o. in an amount of about 1.0 to about 10 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) in an amount of about 100 to 200 mg per dose, wherein each dose is administered twice a day, and (b) Letrozole p.o. in an amount of about 2.5 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) orally in an amount of about 50 mg to about 300 mg per dose wherein each dose is administered twice a day, and (b) Exemestane p.o. in an amount of about 10 to about 50 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) in an amount of about 100 to 200 mg per dose, wherein each dose is administered twice a day, and (b) Exemestane in an amount of about 25 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) orally in an amount of about 50 mg to about 300 mg per dose wherein each dose is administered twice a day, and (b) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (a) at least one compound of formula 1.0 (usually one) orally in an amount of about 100 to 200 mg per dose, wherein each dose is administered twice a day, and (b) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (a) at least one compound of formula 1.0 (usually one) p.o. in an amount of about 50 mg to about 300 mg per dose wherein each dose is administered twice a day, and (b) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) 1.0 p.o. in an amount of about 100 to 200 mg per dose, wherein each dose is administered twice a day, and (b) Tamoxifen p.o. in an amount of about 20 mg per dose wherein each dose is given once a day.

In other embodiments of the invention breast cancer is treated in a patient in need of such treatment wherein said treatment comprises the administration of at least one compound of formula 1.0 (usually one), one of the aromatase inhibitors (e.g., Anastrozole, Letrozole, or Exemestane, and preferably Anastrozole), and one of the antiestrogens (e.g., Fulvestrant or Tamoxifen), wherein the compounds of formula 1.0, aromatase inhibitor and antiestrogen are administered in the dosages described above.

Thus, for example in another embodiment of this invention breast cancer is treated (or prevented) in a patient in need of such treatment wherein said treatment comprises administering to said patient of: (a) at least one compound of formula 1.0 (usually one) p.o. in an amount of about 50 mg to about 300 mg per dose wherein each dose is administered twice a day, (b) Anastrozole p.o. in an amount of about 0.5 to about 10 mg per dose wherein each dose is given once a day, and (c) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (a) at least one compound of formula 1.0 (usually one) p.o. in an amount of about 100 to 200 mg per dose, wherein each dose is administered twice a day, (b) Anastrozole p.o. in an amount of about 1.0 mg per dose wherein each dose is given once a day, and (c) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (a) at least one compound of formula 1.0 (usually one) p.o. in an amount of about 50 mg to about 300 mg per dose wherein each dose is administered twice a day, (b) Letrozole p.o in an amount of about 1.0 to about 10 mg per dose wherein each dose is given once a day, and (c) Fulvestrant in an amount of about 100 to about 1000 mg per dose wherein each dose is given once a month.

In another embodiment of this invention breast cancer is treated (or prevented) in a patient in need of such treatment wherein said treatment comprises administering to said patient: (a) at least one compound of formula 1.0 (usually one) p.o. in an amount of about 100 to 200 mg per dose, wherein each dose is administered twice a day, (b) Letrozole p.o. in an amount of about 2.5 mg per dose wherein each dose is given once a day, and (c) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (a) at least one compound of formula 1.0 (usually one) p.o. in an amount of about 50 mg to about 300 mg per dose wherein each dose is administered twice a day, (b) Exemestane p.o. in an amount of about 10 to about 50 mg per dose wherein each dose is given once a day, and (c) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (a) at least one compound of formula 1.0 (usually one) p.o. in an amount of about 100 to 200 mg per dose, wherein each dose is administered twice a day, (b) Exemestane p.o. in an amount of about 25 mg per dose wherein each dose is given once a day, and (c) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (a) at least one compound of formula 1.0 (usually one) p.o. in an amount of about 50 mg to about 300 mg per dose wherein each dose is administered twice a day, (b) Anastrozole p.o. in an amount of about 0.5 to about 10 mg per dose wherein each dose is given once a day, and (c) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) p.o. in an amount of about 100 to 200 mg per dose, wherein each dose is administered twice a day, (b) Anastrozole p.o. in an amount of about 1.0 mg per dose wherein each dose is given once a day, and (c) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) p.o. in an amount of about 50 mg to about 300 mg per dose wherein each dose is administered twice a day, (b) Letrozole p.o. in an amount of about 1.0 to about 10 mg per dose wherein each dose is given once a day, and (c) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) p.o. in an amount of about 100 to 200 mg per dose, wherein each dose is administered twice a day, (b) Letrozole p.o. in an amount of about 2.5 mg per dose wherein each dose is given once a day, and (c) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) 1.0 p.o. in an amount of about 50 mg to about 300 mg per dose wherein each dose is administered twice a day, (b) Exemestane p.o. in an amount of about 10 to about 50 mg per dose wherein each dose is given once a day, and (b) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (a) at least one compound of formula 1.0 (usually one) p.o. in an amount of about 100 to 200 mg per dose, wherein each dose is administered twice a day, (b) Exemestane p.o. in an amount of about 25 mg per dose wherein each dose is given once a day, and (c) Tamoxifen p.o. in an amount of about 20 mg per dose wherein each dose is given once a day.

Those skilled in the art will appreciate that when other combinations of antihormonal agents are used, the individual antihormonal agent is used in the amounts specified above for that individual antihormonal agent.

Other embodiments of the treatment of Breast Cancer are directed to the methods of treating Breast Cancer described above wherein the compounds of formula 1.0 are dosed twice a day in an amount of about 100 mg per dose.

Other embodiments of the treatment of Breast Cancer are directed to the methods of treating Breast Cancer described above wherein the compounds of formula 1.0 are dosed twice a day in an amount of about 200 mg per dose.

Other embodiments of the treatment of Breast Cancer are directed to the methods of treating Breast Cancer described above wherein a chemotherapeutic agent is administered in addition to the compounds of formula 1.0 and antihormonal agent (or antihormonal agents). In these embodiments the dosage ranges of the compound of formula 1.0 and antihormonal agents are as those described above in the combination therapies, or those described above for the individual compound of formula 1.0 and antihormonal agents, and the dosages of the chemotherapeutic agents are those described above for the individual chemotherapeutic agent. The dosages for the chemotherapeutic agents are well known in the art.

Other embodiments of this invention are directed to pharmaceutical compositions comprising the compounds of formula 1.0 and at least one antihormonal agent and a pharmaceutically acceptable carrier.

Other embodiments of this invention are directed to pharmaceutical compositions comprising the compounds of formula 1.0, at least one antihormonal agent, at least one chemotherapeutic agent, and a pharmaceutically acceptable carrier.

Other embodiments of this invention are directed to pharmaceutical compositions comprising the compounds of formula 1.0, at least one chemotherapeutic agent, and a pharmaceutically acceptable carrier.

Those skilled in the art will recognize that the actual dosages and protocols for administration employed in the methods of this invention may be varied according to the judgment of the skilled clinician. A determination to vary the dosages and protocols for administration may be made after the skilled clinician takes into account such factors as the patient's age, condition and size, as well as the severity of the cancer being treated and the response of the patient to the treatment.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

In the embodiments of this invention wherein a platinum coordinator compound is used as well as at least one other antineoplastic agent, and these drugs are administered consecutively, the platinum coordinator compound is generally administered after the other antineoplastic agents have been administered.

Other embodiments of this invention include the administration of a therapeutically effective amount of radiation to the patient in addition to the administration of the compounds of formula 1.0 and antineoplastic agents in the embodiments described above. Radiation is administered according to techniques and protocols well know to those skilled in the art.

Another embodiment of this invention is directed to a pharmaceutical composition comprising at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising at least one compound of formula 1.0 (usually one) and at least two different antineoplastic agents and a pharmaceutically acceptable carrier for intravenous administration. In one embodiment, the pharmaceutically acceptable carrier is an isotonic saline solution (0.9% NaCl) or a dextrose solution (e.g., 5% dextrose).

Another embodiment of this invention is directed to a pharmaceutical composition comprising at least one compound of formula 1.0 (usually one) and at least one antineoplastic agent and a pharmaceutically acceptable carrier for intravenous administration. In one embodiment, the pharmaceutically acceptable carrier is an isotonic saline solution (0.9% NaCl) or a dextrose solution (e.g., 5% dextrose).

Those skilled in the art will appreciate that the compounds (drugs) used in the methods of this invention are available to the skilled clinician in pharmaceutical compositions (dosage forms) from the manufacturer and are used in those compositions. So, the recitation of the compound or class of compounds in the above described methods can be replaced with a recitation of a pharmaceutical composition comprising the particular compound or class of compounds. For example, the embodiment directed to a method of treating cancer comprising administering to a patient in need of such treatment therapeutically effective amounts of the compounds of formula 1.0, a taxane, and a platinum coordination compound, includes within its scope a method of treating cancer comprising administering to a patient in need of such treatment therapeutically effective amounts of a pharmaceutical composition comprising at least one compound of formula 1.0 (usually one), a pharmaceutical composition comprising a taxane, and a pharmaceutical composition comprising a platinum coordination compound.

The actual dosage employed may be varied depending upon the requirements of the patient and the severity of the condition being treated. Determination of the proper dosage for a particular situation is within the skill of the art.

The amount and frequency of administration of the FPT compounds of this invention and the antineoplastic agents will be regulated according to the judgment of the attending clinician (physician) considering such factors as age, condition and size of the patient as well as severity of the cancer being treated.

The antineoplastic agent can be administered according to therapeutic protocols well known in the art. It will be apparent to those skilled in the art that the administration of the antineoplastic agent can be varied depending on the cancer being treated and the known effects of the antineoplastic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of antineoplastic agent will depend upon the diagnosis of the attending physicians and their judgment of the condition of the patient and the appropriate treatment protocol.

The determination of the order of administration, and the number of repetitions of administration of the antineoplastic agent during a treatment protocol, is well within the knowledge of the skilled physician after evaluation of the cancer being treated and the condition of the patient.

Thus, in accordance with experience and knowledge, the practicing physician can modify each protocol for the administration of an antineoplastic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

CHEMOTHERAPEUTIC AGENTS

Classes of compounds that can be used as chemotherapeutic agents (antineoplastic agent/microtubule affecting agents) include but are not limited to: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), paclitaxel derivatives (e.g. taxotere), Mithramycin, Deoxycoformycin, Mitomycin-C, L-Asparaginase, Interferons (especially IFN-a), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Other chemotherapeutics include Navelbene, CPT-11, Anastrazole, Letrazole, Capecitabinbe, Reloxafine, and Droloxafine.

Particularly preferred are the antineoplastic agents selected from Cyclophasphamide, 5-Fluorouracil, Temozolomide, Vincristine, Cisplatin, Carboplatin, and Gemcitabine. Most preferably, the antineoplastic agent is selected from Gemcitabine, Cisplatin and Carboplatin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), 57th Edition (Thomson PDR, Montvale, N.J. 07645-1742); the disclosure of which is incorporated herein by reference thereto.

MICROTUBULE AFFECTING AGENTS

As used herein, a microtubule affecting agent (e.g., paclitaxel, a paclitaxel derivative or a paclitaxel-like compound) is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), paclitaxel derivatives (e.g., Taxotere, NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Particularly preferred agents are compounds with paclitaxel-like activity. These include, but are not limited to paclitaxel and paclitaxel derivatives (paclitaxel-like compounds) and analogues. Paclitaxel and its derivatives (e.g. Taxol and Taxotere) are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz (1992) Trends Pharmacol. Sci. 13: 134-146, Rowinsky (1990) J. Natl. Canc. Inst. 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. For example, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) J. Molec. Biol., 89: 737-758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (cited above).

The compounds of this invention can be used according to the methods described in U.S. 2003/0185831 published Oct. 2, 2003, the disclosure of which is incorporated herein by reference thereto.

Compounds of the invention can be prepared according to the procedures described below and the procedures described in: WO 95/10516 (published Apr. 20, 1995), WO 96/31478 (published Oct. 10, 1996), WO 97/23478 (published Jul. 3, 1997, see also U.S. Pat. No. 5,874,442 issued Feb. 23, 1999), U.S. Pat. No. 5,719,148 issued Feb. 17, 1998, WO 98/57960 (published Dec. 23, 1998), U.S. Pat. No. 6,362,188 (issued Mar. 26, 2002), and U.S. Pat. No. 6,372,747 (issued Apr. 16, 2002); the disclosures of each being incorporated herein by reference thereto.

Compounds useful in this invention are exemplified by the following process schemes and examples, these process schemes and examples should not be construed to limit the scope of the disclosure. Alternative mechanistic pathways and analogous structures within the scope of the invention may be apparent to those skilled in the art.

Compounds of the invention can be prepared according to the reaction schemes described below.

The synthesis of carboxylic acid methyl ester (E) begins with N-cbz,N-boc piperazine carboxylic acid (A)(U.S. Pat. No. 6,362,188 B1) (Scheme 1). Reaction with methyl iodide and cesium carbonate in DMF followed by hydrogenation over Pd—C selectively removes the Cbz group and the resulting amino acid methyl ester was coupled with the desired tricyclic chloride (Scheme 2)(described in U.S. Pat. No. 6,214,827 B1). Compounds containing various functional groups can also be prepared. The distereomers can be typically separated using conventional methods, such as chromatography (Scheme 3). The lithium salts, prepared by treating the esters with lithium hydroxide in MeOH, were coupled with the desired amines (described in U.S. Pat. Nos. 6,362,188 and 6,372,747) under standard conditions (DEC, HOBT, NMM) to give the amides (Scheme 4). Alternatively, the piperazine amide (described in U.S. Pat. No. 6,362,188) can be selectively alkylated by the desired tricyclic chloride (TEA, DMF, rt, 48 hours). At this stage, the free amine can be acylated, alkylated, or amidated under conditions obvious to one skilled in the art. Chiral HPLC separation can be employed to readily resolve the C-11 distereomers. (Scheme 5)

Scheme 1
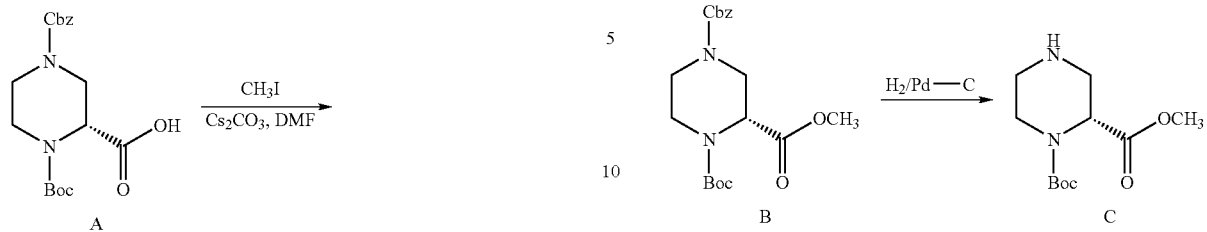
Scheme 2
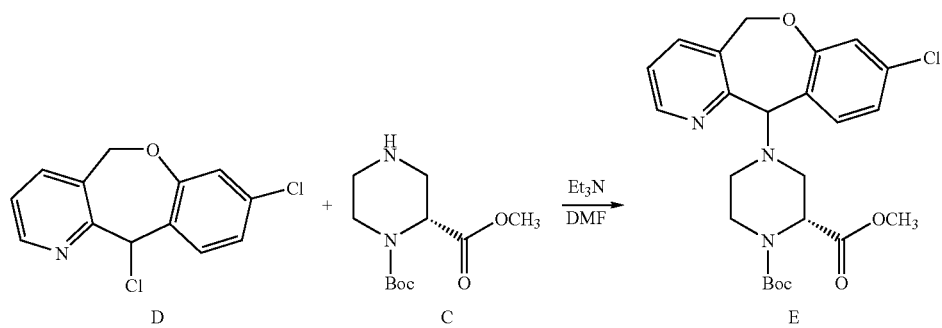
Scheme 3
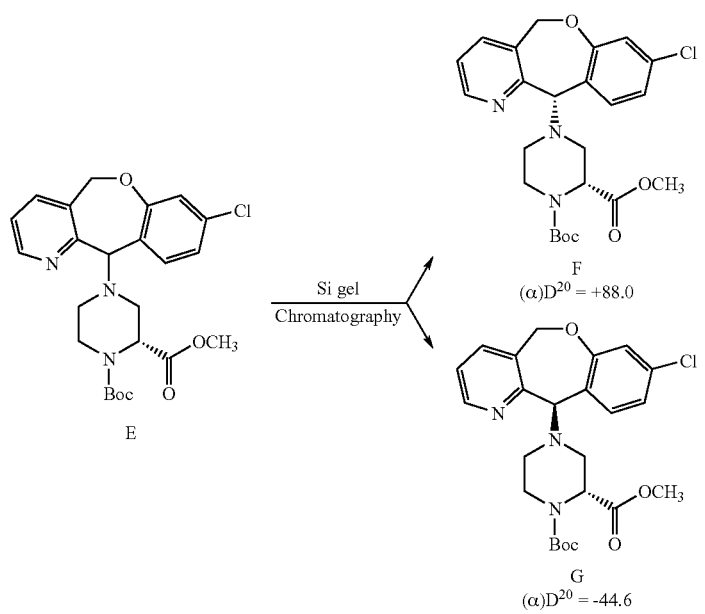

Scheme 4
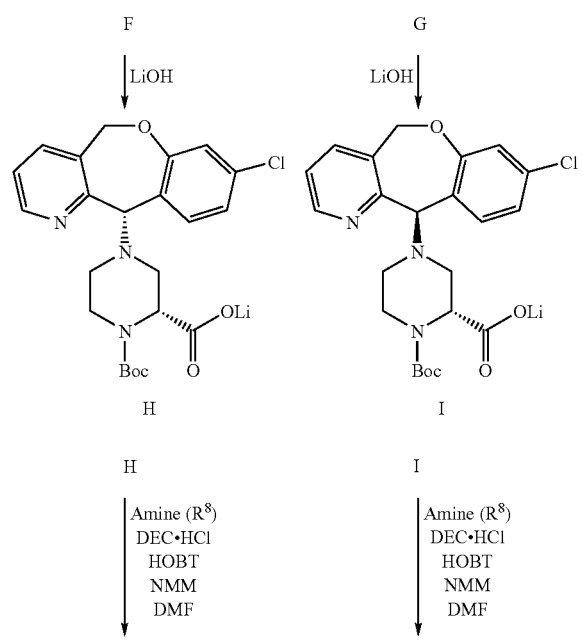
Scheme 5
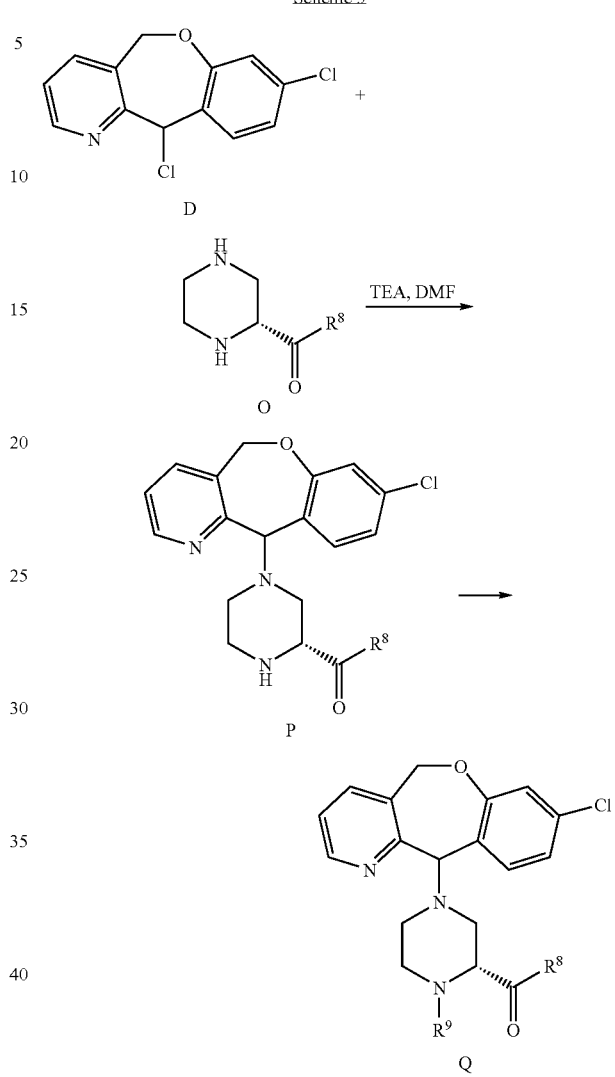
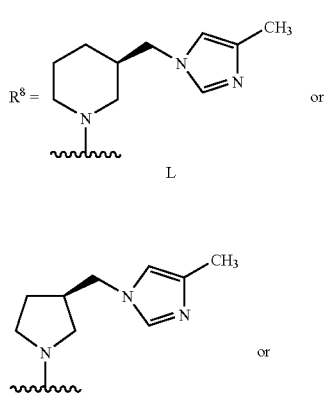
Compounds of this invention are exemplified in the following examples, which should not be construed as limiting the scope of the disclosure. Alternative mechanistic pathways and analogous structures within the scope of the invention may be apparent to those skilled in the art.
PREPARATIVE EXAMPLE 1
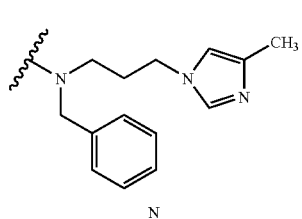
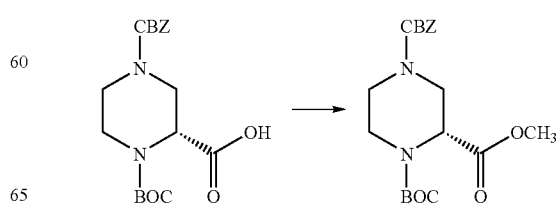

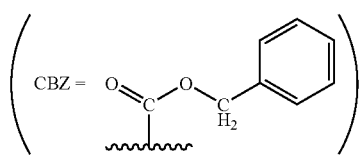

(2R)-1-[(tert-butyl)oxycarbonyl]-4-[benzyloxycarbonyl] piperazine-2-carboxylic acid (see Preparative Example 49 in U.S. Pat. No. 6,372,747) (2.9 gm, 7.96 mmol) was stirred in DMF (50 mL), methyl iodide (1.5 mL, 23.81 mmol), and cesium carbonate (7.78 gm, 23.87 mmol) at room temperature for three hours and concentrated in vacuo. The residue was diluted with water and extracted with methylene chloride. The organics were dried over MgSO$_4$, filtered and concentrated under reduced pressure. The crude product was purified by flash chromatography using 20% EtOAc in hexane solution as eluant to give a white foam (1.9 gm, 63% yield), FABMS: MH+=379.

PREPARATIVE EXAMPLE 2

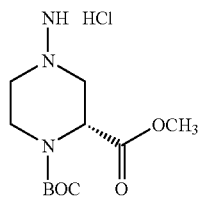

The title compound from Preparative Example 1 (1.85 gm) was dissolved in MeOH (25 mL) and 1N HCl (0.5 mL) in a hydrogenation vessel. The vessel was flushed with N$_2$ and 10% Pd/C (0.38 gm, 50% weight with water) was added. The mixture was hydrogenated at 55 psi of H$_2$ for 18 hours. When the reaction was complete (TLC, 25% EtOAc/Hexane) the catalyst was filtered off and the filtrate was evaporated to dryness to give the title compound (1.3 gm).

PREPARATIVE EXAMPLE 3

1,1-Dimethyl-4-(8-chloro-5,11-dihydro-[1]benzoxepino[4,3-b]pyridin-11-yl)-2(R)-(methoxycarbonyl) piperazinecarboxylate

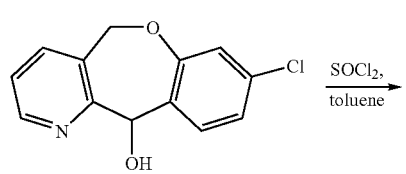

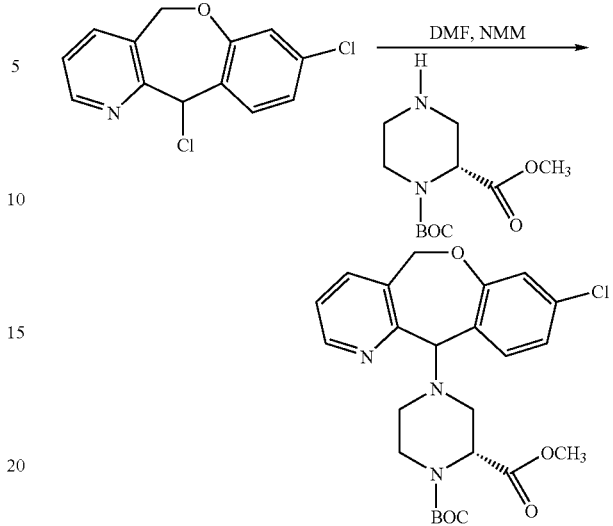

The tricyclic alcohol (Biorg. & Med. Chem. Lett. 2521, 1998) (7.01 gm, 28.3 mmol) was dissolved in toluene (100 mL) and SOCl$_2$ (4 mL) was added while stirring under a dry N$_2$ atmosphere. After 4 hrs, the mixture was evaporated to give a gum which was extracted with EtOAc and washed with 10% NaOH. The organics were dried over MgSO$_4$, filtered and concentrated under reduced pressure to give a foamy solid. The resulting chloro-trycyclic compound was dissolved in dry DMF (100 mL) and the title compound from Preparative Example 2 (7.94 gm, 28.29 mmol) was added followed by 4-methyl morpholine 15.54 mL, 141 mmol) and the mixture was stirred at room temperature under N$_2$. After 24 hrs, the reaction mixture was concentrated and the residue dissolved in EtOAc and washed with brine. The organics were dried over MgSO$_4$, filtered and concentrated under reduced pressure to give the title compound (9.5 g)

PREPARATIVE EXAMPLES 4 AND 5

The title compound from Preparative Example 3 was separated into individual (S, 1.76 gm) and (R, 1.73 gm)—isomers by flash chromatography using 10% EtOAc in CH$_2$Cl$_2$ solution as eluant.

PREPARATIVE EXAMPLE 4

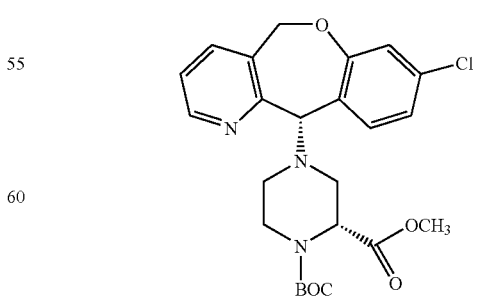

(11-(S)-isomer: $[\alpha]_D^{20\ °C}$=+88.0° (5.64 mg in 2.0 mL MeOH); LCMS: MH+=474.

PREPARATIVE EXAMPLE 5

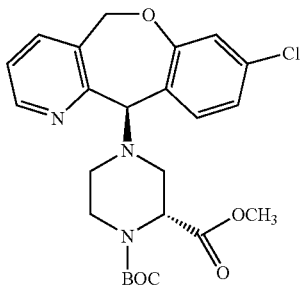

(11-(R)-isomer: $[\alpha]_D^{20°\ C}$=-44.6° (3.8 mg in 2.0 mL MeOH); LCMS: MH+=474.

PREPARATIVE EXAMPLE 6

1,1-Dimethyl-4-(8-chloro-5,11-dihydro-[1]benzoxepino[4,3-b]pyridin-11(S)-yl)-2(R)-carbonyl-piperazine lithiumcarboxylate

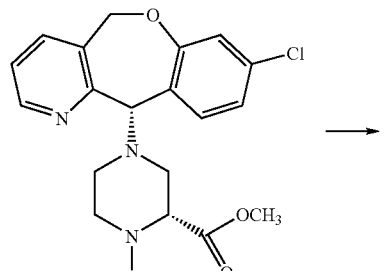

The title compound from Preparative Example 4 (1.1 gm) was dissolved in MeOH (20 mL) and 1N LiOH (4.64 mL) was added and heated at 60° C. overnight. Extracted with CH$_2$Cl$_2$ and washed with brine, dried over MgSO$_4$ and evaporated to dryness to give the title compound (0.853 gm)

PREPARATIVE EXAMPLE 7

1,1-Dimethyl-4-(8-chloro-5,11-dihydro-[1]benzoxepino[4,3-b]pyridin-11(R)-yl)-2(R)-carbonyl)piperazine lithiumcarboxylate

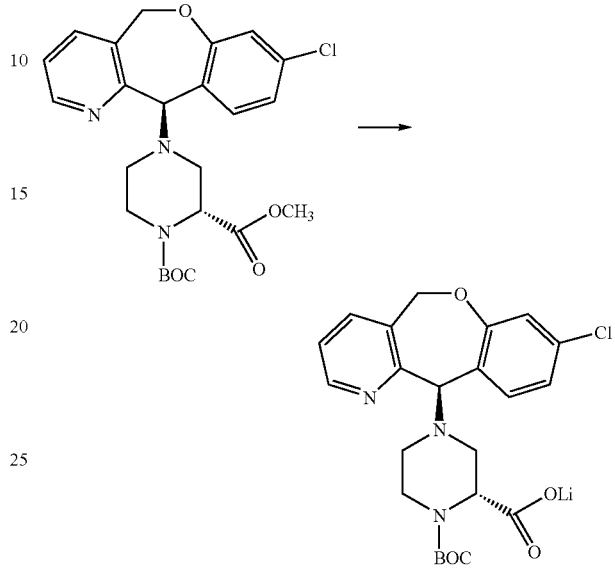

By essentially the same procedure as set forth in Preparative Example 6, the title compound was prepared using the material from Preparative Example 5.

PREPARATIVE EXAMPLE 8

1,1-Dimethyl-4-(8-chloro-5,11-dihydro-[1]benzoxepino[4,3-b]pyridin-11(S)-yl)-2-[[3(S)-(4-methyl-1H-imidazol-1yl)methyl]-1-piperidinyl]carbonyl]-1-piperazinecarboxylate

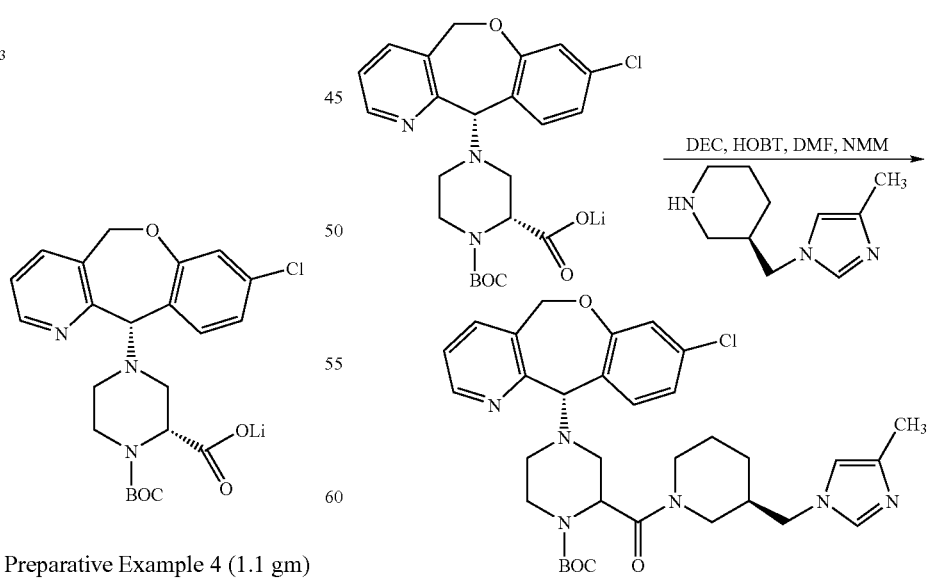

By essentially same procedure set forth in Example 1 except using 1 (3R) (3-piperidyl)methyl)-4-methyl imidazole (see U.S. Pat. No. 6,362,188), the title compound was prepared.

PREPARATIVE EXAMPLE 9

1,1-Dimethyl-4-(8-chloro-5,11-dihydro-[1]benzoxepino[4,3-b]pyridin-11(R)-yl)-2-[[3(S)-(4-methyl-1H-imidazol-1yl)methyl]-1-piperidinyl]carbonyl]-1-piperazinecarboxylate

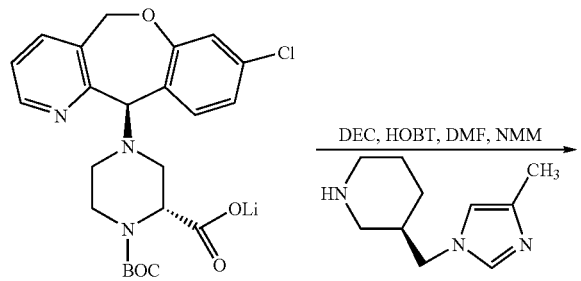

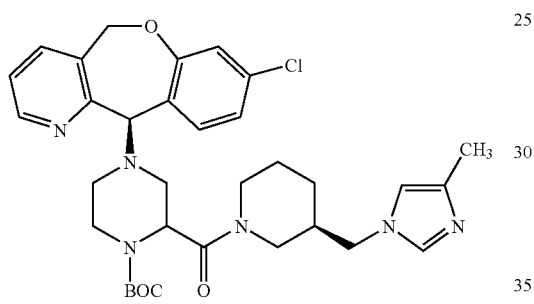

By essentially same procedure set forth in Example 1 except using 1 (3R) (3-piperidyl)methyl)-4-methyl imidazole (see U.S. Pat. No. 6,362,188) the title compound was prepared.

PREPARATIVE EXAMPLE 10

1,1-Dimethyl-4-(8-chloro-5,11-dihydro-[1]benzoxepino[4,3-b]pyridin-11(S)-yl)-2-[[3(S)-(4-methyl-1H-imidazol-1yl)methyl]-1-pyrrolidinyl]carbonyl]-1-piperazinecarboxylate

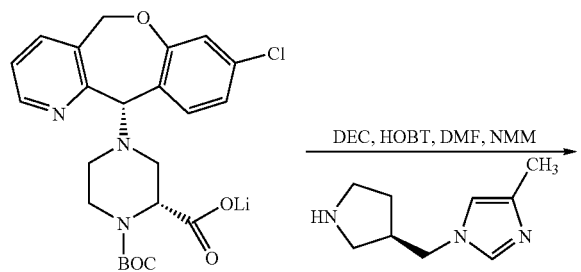

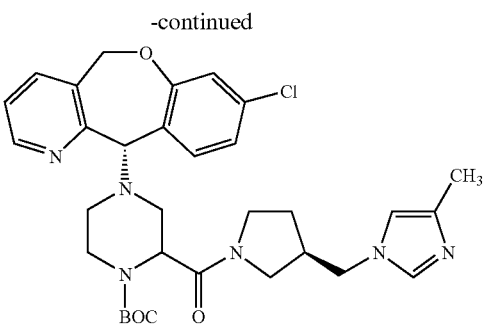

By essentially same procedure set forth in Preparative Example 8 except using 1(3R) (3-pyrrolidinyl)methyl)-4-methyl imidazole (see U.S. Pat. No. 6,362,188) the title compound was prepared.

PREPARATIVE EXAMPLE 11

1,1-Dimethyl-4-(8-chloro-5,11-dihydro-[1]benzoxepino[4,3-b]pyridin-11(R)-yl)-2-[[3(S)-(4-methyl-1H-imidazol-1yl)methyl]-1-pyrrolidinyl]carbonyl]-1-piperazinecarboxylate

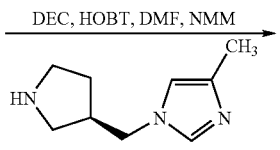

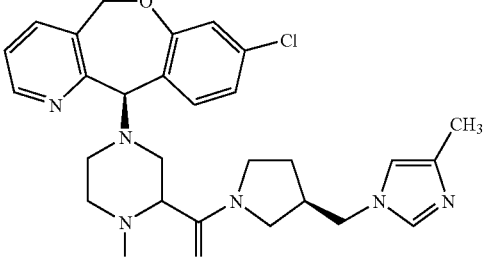

By essentially same procedure set forth in Preparative Example 9 except using 1(3R) (3-pyrrolidinyl)methyl)-4-methyl imidazole (see U.S. Pat. No. 6,362,188) the title compound was prepared.

PREPARATIVE EXAMPLE 12

Cyclohexyl-4-(8-chloro-5,11-dihydro-[1]benzox-
epino[4,3-b]pyridin-11yl)-2(R)-[[3(S)-(4-methyl-
1H-imidazol-1yl)methyl]-1-pipeidinyl]carbonyl]-1-
piperazinecarboxylate

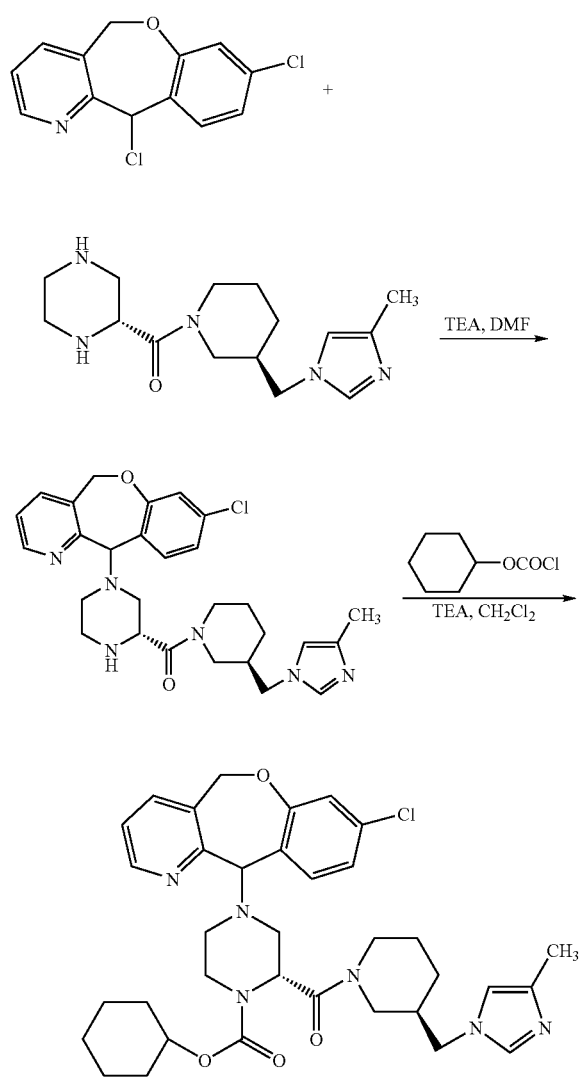

2(R)-2-((3S)-3-((4-methylimidazole)methyl)carbonyl)pi-
parazine (0.136 gm, 1 eq) was added to chloro-tricyclic com-
pound Preparative Example 3 (0.125 gm, 1 eq.) in TEA (5
mL) and DMF (5 mL). The resulting solution was stirred at
room temperature for 72 hours at which time the reaction
mixture was concentrated under reduced pressure. The crude
product without further purification was dissolved in CH$_2$Cl$_2$
(5 mL) and TEA (5 eq) and cyclohexylchloroformate (0.152
gm, 2 eq) was added. The reaction mixture was stirred at room
temperature overnight before adding H2O (15 mL) and
extracting with CH$_2$Cl$_2$ (2×100 mL). The combined organics
were dried over Na$_2$SO$_4$, filtered and concentrated in vavuo.
The crude product was purified by flash chromatography
using 3% (10% NH$_4$OH in MeOH) solution in CH$_2$Cl$_2$ as
eluent to give the title compound (0.14 gm, 46% yield).

EXAMPLE 1

1,1-Dimethyl-4-(8-chloro-5,11-dihydro-[1]benzox-
epino[4,3-b]pyridin-11(S)-yl)-2(R)-[[[3-(4-methyl-
1H-imidazol-1yl)propyl]phenylmethyl)amino]carbo-
nyl]-1-piperazinecarboxylate

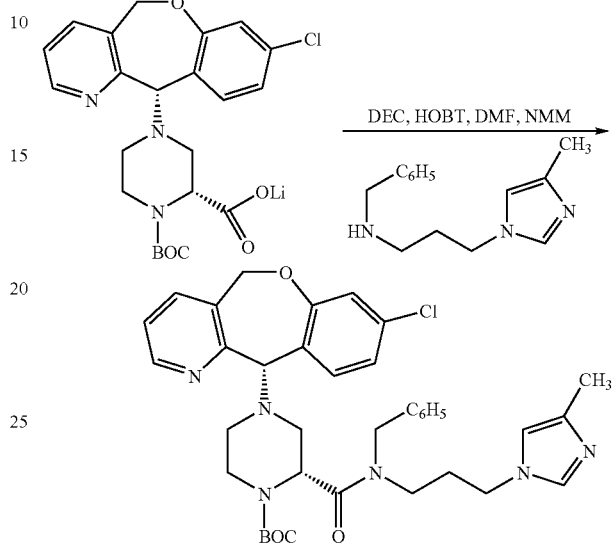

The title compound from Example 6 (0.25 gm, 0.536
mmol) was added to a solution of 4-(4-methyl imidazolyl)
butyl benzylamine (see Preparative Example 85 in U.S. Pat.
No. 6,372,747) (0.124 gm, 0.536 mmol), DEC (0.133 gm,
0.695 mmol), HOBT (0.094 gm, 0.695 mmol) and NMM
(0.27 gm, 2.68 mmol) in DMF (15 mL). The resulting solu-
tion was stirred at room temperature 24 hours. The reaction
mixture was diluted with H$_2$O until precipitation ceased and
the slurry filtered. The precipitate was diluted with CH$_2$Cl$_2$
(50 mL) and washed with water 2×50 mL), dried over MgSO$_4$
and concentrated. The crude product was purified by prep
plate (4×20×20, 1000M) chromatography using with 8%
(10% NH$_4$OH in MeOH) solution in CH$_2$Cl$_2$ as eluent to give
a pale yellow foam (0.056 g). FABMS: MH$^+$=672),
$[\alpha]_D^{20\ C}$=+48.75° (12.3 mg in 2.0 mL MeOH).

EXAMPLE 2

1,1-Dimethyl-4-(8-chloro-5,11-dihydro-[1]benzox-
epino[4,3-b]pyridin-11(R)-yl)-2(R)-[[[3-(4-methyl-
1H-imidazol-1yl)propyl]phenylmethyl)amino]carbo-
nyl]-1-piperazinecarboxylate

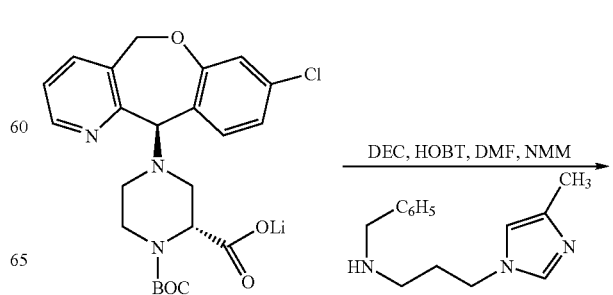

-continued

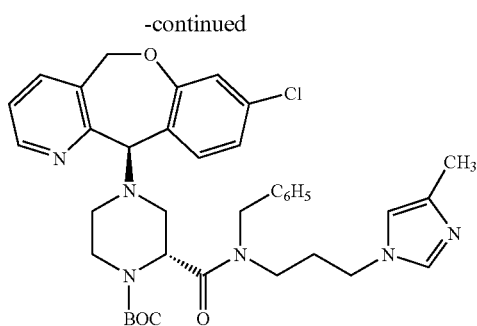

By essentially same procedure set forth in Example 1 except using the title compound from Preparative Example 7, the title compound was prepared. FABMS: MH$^+$=672), $[\alpha]_D^{20°\ C.}$=−41.2° (13.6 mg in 2.0 mL MeOH).

EXAMPLE 3 AND EXAMPLE 4

The title compound from Preparative Example 8 was separated into individual 2S and 2R isomers by Preparative HPLC with a CHIRALPAK AD column using 20% iPrOH in hexanes solution with 0.2% DEA as eluent.

EXAMPLE 3

2R Isomer 1,1-Dimethyl-4-(8-chloro-5,11-dihydro-[1]benzoxepino[4,3-b]pyridin-11(S)-yl)-2(R)-[[3(S)-(4-methyl-1H-imidazol-1yl)methyl]-1-pipeidinyl]carbonyl]-1-piperazinecarboxylate

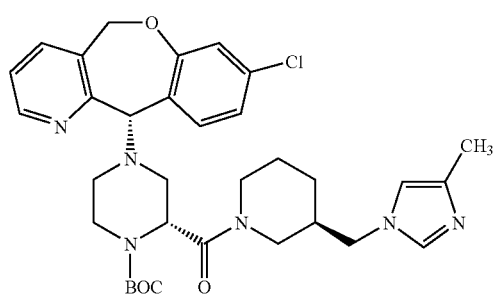

2-(R)-isomer: retention time (analytical)=28.534 minutes; FABMS: MH$^+$=622), $[\alpha]_D^{20°\ C.}$=+84.48° (12.3 mg in 2.0 mL MeOH).

EXAMPLE 4

2S Isomer 1,1-Dimethyl-4-(8-chloro-5,11-dihydro-[1]benzoxepino[4,3-b]pyridin-11(S)-yl)-2(S)-[[3(S)-(4-methyl-1H-imidazol-1yl)methyl]-1-pipeidinyl]carbonyl]-1-piperazinecarboxylate

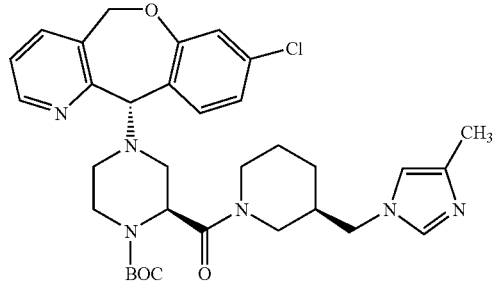

2-(S)-isomer: retention time (analytical)=12.585 minutes; FABMS: MH$^+$=622), $[\alpha]_D^{20°\ C.}$=−23.93° (13.3 mg in 2.0 mL MeOH).

EXAMPLE 5 AND EXAMPLE 6

The title compound from Preparative Example 9 was separated into individual 2S and 2R isomers by Preparative HPLC with a CHIRALPAK AD column using 20% iPrOH in hexanes solution with 0.2% DEA as eluent.

EXAMPLE 5

2R Isomer 1,1-Dimethyl-4-(8-chloro-5,11-dihydro-[1]benzoxepino[4,3-b]pyridin-11(R)-yl)-2(R)-[[3(S)-(4-methyl-1H-imidazol-1yl)methyl]-1-pipeidinyl]carbonyl]-1-piperazinecarboxylate

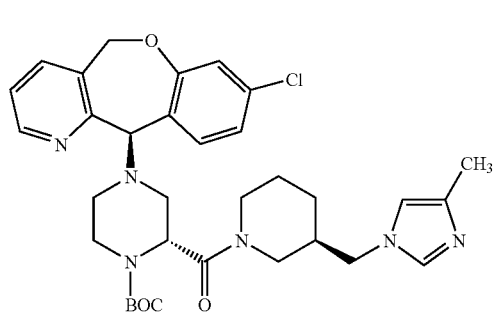

2-(R)-isomer: retention time (analytical)=12.1 minutes; FABMS: MH$^+$=622), $[\alpha]_D^{20°\ C.}$=+2.46° (8.2 mg in 2.0 mL MeOH).

EXAMPLE 6

2S Isomer 1,1-Dimethyl-4-(8-chloro-5,11-dihydro-[1]benzox-epino[4,3-b]pyridin-11(R)-yl)-2(S)-[[3(S)-(4-methyl-1H-imidazol-1yl)methyl]-1-pipeidinyl]carbonyl]-1-piperazinecarboxylate

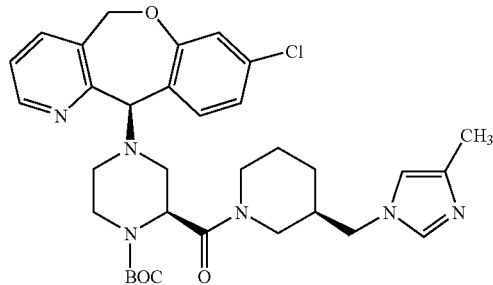

2-(S)-isomer: retention time (analytical)=28.9 minutes; FABMS: MH$^+$=622), $[\alpha]_D^{20°\ C.}$=+2.46° (19.3 mg in 2.0 mL MeOH).

EXAMPLE 7 & EXAMPLE 8

The title compound from Preparative Example 10 was separated into individual 2(S), and 2(R), isomers Prep plate chromatography using 8% (10% NH$_4$OH in MeOH) solution in CH$_2$Cl$_2$ as eluent.

EXAMPLE 7

2R Isomer 1,1-Dimethyl-4-(8-chloro-5,11-dihydro-[1]benzox-epino[4,3-b]pyridin-11(S)-yl)-2(R)-[[3(S)-(4-methyl-1H-imidazol-1yl) methyl]-1-pyrrolidinyl]carbonyl]-1-piperazinecarboxylate

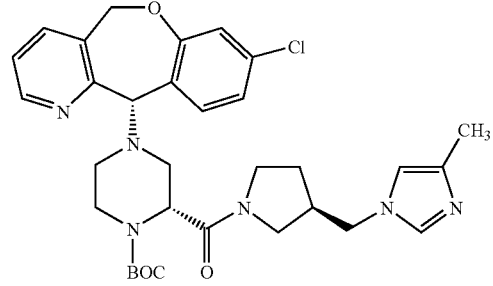

2-(R)-isomer: FABMS: MH$^+$=608), $[\alpha]_D^{20°\ C.}$=−7.21° (8.4 mg in 2.0 mL MeOH).

EXAMPLE 8

2S Isomer 1,1-Dimethyl-4-(8-chloro-5,11-dihydro-[1]benzox-epino[4,3-b]pyridin-11 (S)-yl)-2(S)-[[3(S)-(4-methyl-1H-imidazol-1yl)methyl]-1-pyrrolidinyl]carbonyl]-1-piperazinecarboxylate

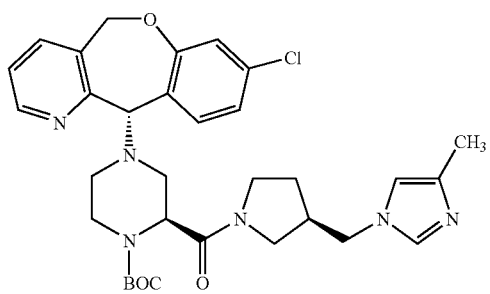

2-(S)-isomer: FABMS: MH$^+$=608), $[\alpha]_D^{20°\ C.}$=+60.06° (10.8 mg in 2.0 mL MeOH).

EXAMPLE 9 & EXAMPLE 10

The title compound from Preparative Example 11 was separated into individual 2(S), and 2(R), isomers Prep plate chromatography using 8% (10% NH$_4$OH in MeOH) solution in CH$_2$Cl$_2$ as eluent.

EXAMPLE 9

2R Isomer 1,1-Dimethyl-4-(8-chloro-5,11-dihydro-[1]benzox-epino[4,3-b]pyridin-11(R)-yl)-2(R)-[[3(S)-(4-methyl-1H-imidazol-1yl)methyl]-1-pyrrolidinyl]carbonyl]-1-piperazinecarboxylate

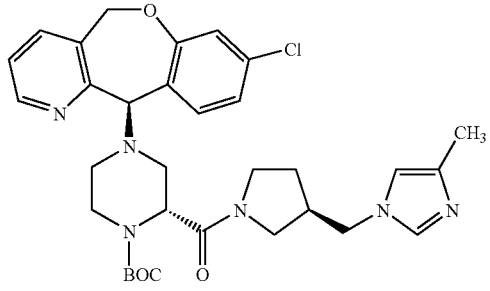

2-(R)-isomer: FABMS: MH$^+$=608), $[\alpha]_D^{20°\ C.}$=−31.67° (12.42 mg in 2.0 mL MeOH).

EXAMPLE 10

2S Isomer 1,1-Dimethyl-4-(8-chloro-5,11-dihydro-[1]benzoxepino[4,3-b]pyridin-11(R)-yl)-2(S)-[[3(S)-(4-methyl-1H-imidazol-1 yl)methyl]-1-pyrrolidinyl]carbonyl]-1-piperazinecarboxylate

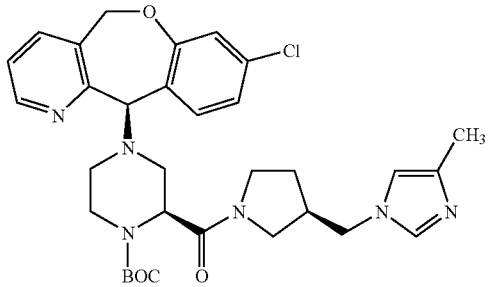

2-(S)-isomer: FABMS: MH+=608), $[\alpha]_D^{20°\ C.}$=+31.63° (10.0 mg in 2.0 mL MeOH).

EXAMPLE 11 AND EXAMPLE 12

The title compound from Preparative Example 12 was separated into individual 11R and 11S isomers by Preparative HPLC with a CHIRALPAK AD column using 20% iPrOH in hexanes solution with 0.2% DEA as eluent.

EXAMPLE 11

11R Isomer

Cyclohexyl-4-(8-chloro-5,11-dihydro-[1]benzoxepino[4,3-b]pyridin-11(R)yl)-2(R)-[[3(S)-(4-methyl-1H-imidazol-1yl)methyl]-1-pipeidinyl]carbonyl]-1-piperazinecarboxylate

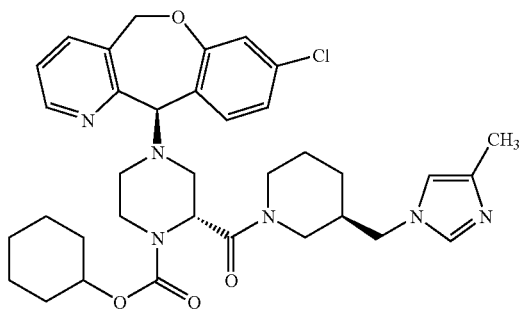

11-(R)-isomer: retention time (analytical)=31.021 minutes; FABMS: MH+=648.

EXAMPLE 12

11S Isomer

Cyclohexyl-4-(8-chloro-5,11-dihydro-[1]benzoxepino[4,3-b]pyridin-11(S)yl)-2(R)-[[3(S)-(4-methyl-1H-imidazol-1yl)methyl]-1-pipeidinyl]carbonyl]-1-piperazinecarboxylate

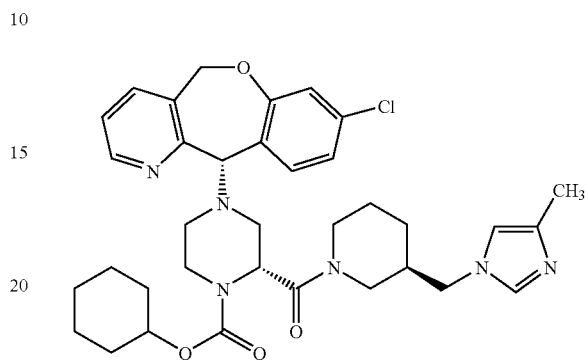

11-(S)-isomer: retention time (analytical)=38.891 minutes; FABMS: MH+=648.

Assay

FPT IC$_{50}$ Assay

FPT activity was determined by measuring the transfer of [$^3$H] farnesyl from [$^3$H] farnesyl pyrophosphate to a biotinylated peptide derived from the C-terminus of H-ras (biotin-CVLS). The reaction mixture contains: 50 mM Tris pH7.7, 5 mM MgCl$_2$, 5 µM Zn$^{++}$, 5 mM DTT, 0.1% Triton-X, 0.05 µM peptide, 0.03 nM purified human farnesyl protein transferase, 0.180 µM [$^3$H] farnesyl pyrophosphate, plus the indicated concentration of tricyclic compound or vehicle control in a total volume of 100 µl. The reaction was incubated in a Vortemp shaking incubator at 37° C., 45 RPM for 60 minutes and stopped with 150 µl of 0.25 M EDTA containing 0.5% BSA and 1.3 mg/ml Streptavidin SPA beads. Radioactivity was measured in a Wallach 1450 Microbeta liquid scintillation counter. Percent inhibition was calculated relative to the vehicle control.

Additional Assays

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of farnesyl transferase inhibitor as the top layer. After the top layer is solidified, plates can be incubated for 10-16 days at 37° C. under 5% CO$_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the $IC_{50}$'s can be determined.

The final compounds of Examples 1 to 12 had an FPT $IC_{50}$ within the range of 0.12 nM to >16 nM. The final compounds of Examples 1 to 10 had a Soft Agar $IC_{50}$ within the range of <5 nM to >50 nM.

The final compounds of Examples 1 to 6, 11 and 12 had an FPT $IC_{50}$ within the range of 0.12 nM to 3 nM. The final compounds of Examples 1 to 6 had a Soft Agar $IC_{50}$ within the range of <5 nM to 28 nM.

The final compounds of Examples 2 to 6 and 11 had an FPT $IC_{50}$ within the range of 0.12 nM to 1 nM. The final compounds of Examples 2 to 6 had a Soft Agar $IC_{50}$ of <5 nM.

The compound of Example 1 had an FPT $IC_{50}$ of 3.0 nM and a Soft Agar $IC_{50}$ of 28.0 nM.

The compound of Example 4 had an FPT $IC_{50}$ of 0.12 nM and a Soft Agar $IC_{50}$ of <5.0 nM. The compound of Example 11 had an FPT $IC_{50}$ of 0.16 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., which is incorporated by reference herein.

Liquid form preparations include solutions, suspensions and emulsions. As an example, water or water-propylene glycol solutions for parenteral injection or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations, which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

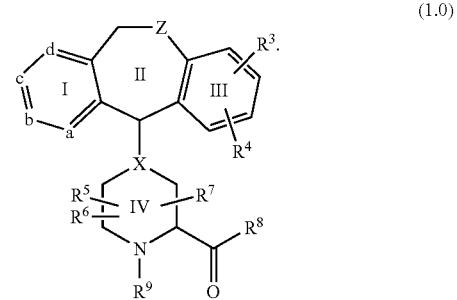

(1.0)

or the pharmaceutically acceptable salts thereof, wherein:
one of a, b, c and d represents N or $N^+O^-$, and the remaining a, b, c and d groups represent $CR^1$ or $CR^2$; or
each of a, b, c, and d are independently selected from the group consisting of: $CR^1$ and $CR^2$;
each $R^1$ and each $R^2$ is independently selected from the group consisting of: H, halo, —$CF_3$, —$OR^{10}$, —$COR^{10}$, —$SR^{10}$, —$S(O)_tR^{11}$ (wherein t is 0, 1 or 2), —$N(R^{10})_2$, —$NO_2$, —$OC(O)R^{10}$, —$CO_2R^{10}$, —$OCO_2R^{11}$, —CN, —$NR^{10}COOR^{11}$, —$SR^{11}C(O)OR^{11}$, $SR^{11}N(R^{75})_2$ (provided that $R^{11}$ in —$SR^{11}N(R^{75})_2$ is not —$CH_2$—) wherein each $R^{75}$ is independently selected from H or —$C(O)OR^{11}$, benzotriazol-1-yloxy, tetrazol-5-ylthio, substituted tetrazol-5-ylthio, alkynyl, alkenyl and alkyl, said alkyl or alkenyl group optionally being substituted with halo, —$OR^{10}$ or —$CO_2R^{10}$;
$R^3$ and $R^4$ are the same or different and each independently represents H, any of the substituents of $R^1$ and $R^2$, or $R^3$ and $R^4$ taken together represent a saturated or unsaturated $C_5$-$C_7$ fused ring to the benzene ring (Ring III);
$R^5$, $R^6$, and $R^7$ each independently represents H, —$CF_3$, —$COR^{10}$, alkyl or aryl, said alkyl or aryl optionally being substituted with one or more substituents selected from the group consisting of: —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, $OCO_2R^{11}$, —$CO_2R^{10}$, and —$OPO_3R^{10}$, or $R^5$ is combined with $R^6$ to represent =O or =S; provided that for the groups —$OR^{10}$, —$SR^{10}$, and —$N(R^{10})_2$ $R^{10}$ is not H;
$R^{10}$ represents H, alkyl, aryl, or aralkyl;
$R^{11}$ represents alkyl or aryl;

X represents N, CH or C, and when X is C the optional bond (represented by the dotted line) to carbon atom 11 is present, and when X is CH the optional bond (represented by the dotted line) to carbon atom 11 is absent;

Z is —O—;

$R^8$ represents a heterocyclic ring selected from the group consisting of:

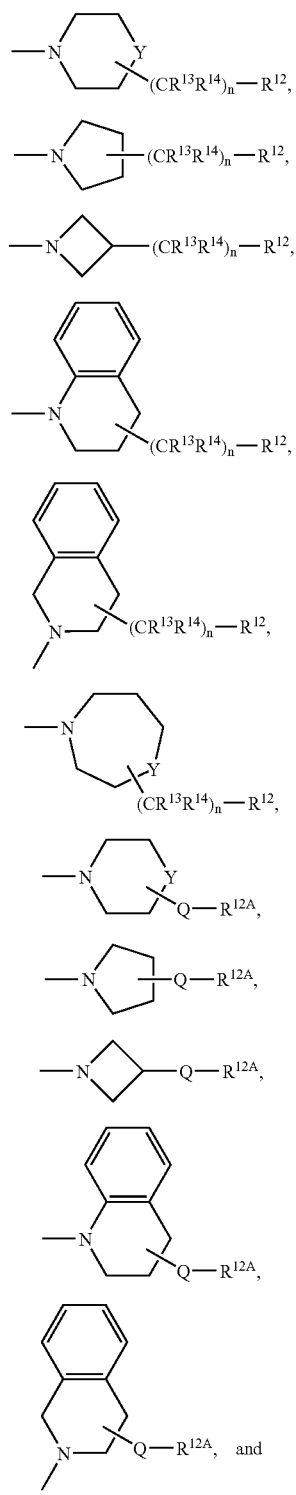

(2.0)
(3.0)
(4.0)
(5.0)
(6.0)
(7.0)
(2.1)
(3.1)
(4.1)
(5.1)
(6.1)

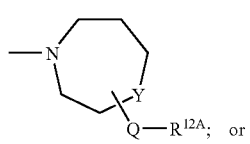

(7.1)

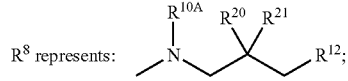

(8.0)

said $R^8$ heterocyclic rings 2.0 to 7.0 and 2.1 to 7.1 being optionally substituted with one or more substituents independently selected from the group consisting of:
(a) alkyl;
(b) substituted alkyl wherein said substituents are selected from the group consisting of: halo, aryl, —$OR^{15}$, —$N(R^{15})_2$, heteroaryl, heterocycloalkyl, and cycloalkyl, wherein each $R^{15}$ group is the same or different, provided that said optional substituent is not bound to a carbon atom that is adjacent to an oxygen or nitrogen atom, and wherein $R^{15}$ is selected from the group consisting of: H, alkyl, aryl, arylalkyl, heteroaryl, heteroarylalkyl, cycloalkyl, and cycloalkylalkyl;
(c) hydroxyl, with the proviso that carbon atoms adjacent to the nitrogen, sulfur or oxygen atoms of the ring are not substituted with hydroxyl;
(d) alkyloxy; and
(e) arylalkyloxy;

Y represents —$CH_2$—, —$NR^{16}$—, —O—, —S—, —S(O)—, or —$S(O_2)$— wherein $R^{16}$ is selected from the group consisting of: H, alkyl, cycloalkyl, cycloalkylalkyl, aryl, arylalkyl, heteroaryl, heteroarylalkyl, acyl, aroyl, carbamoyl, carboxamido, alkylsulfonyl, arylsulfonyl, arylalkylsulfonyl, sulfonamido, alkylsulfonamido, arylsulfonamido and arylalkylsulfonamido;

n is 0 to 6;

Q represents —O— or —N—, provided that Q is not adjacent to a heteroatom in the heterocycloalkyl rings of 2.1, 3.1, 4.1, 5.1, 6.1 and 7.1;

$R^{10A}$ is selected from the group consisting of: H, $C_3$ to $C_4$ alkyl, aryl, arylalkyl, heteroaryl, heteroarylalkyl, cycloalkyl, cycloalkylalkyl, substituted alkyl, substituted aryl, substituted arylalkyl, substituted heteroaryl, substituted heteroarylalkyl, substituted cycloalkyl, and substituted cycloalkylalkyl;

$R^{12}$ is selected from the group consisting of:

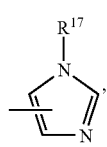

(9.0)

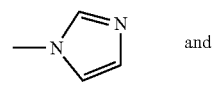

(10.0)

and

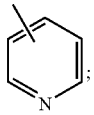
(11.0)

wherein $R^{17}$ is selected from the group consisting of: (1) H, (2) alkyl, (3) aryl, (4) arylalkyl, (5) substituted arylalkyl wherein the substituents are selected from the group consisting of: halo and CN, (6) —C(aryl)$_3$, (7) cycloalkyl, (8) substituted alkyl (as defined above in (b)), and (9) cycloalkylalkyl; $R^{12A}$ is selected from the group consisting of: rings 9.0, 9.1 and 11.0, as defined above;

the imidazolyl ring 9.0 and

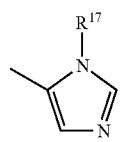
(9.1)

optionally being substituted with one or two substituents, said imidazole ring 10.0 optionally being substituted with 1-3 substituents, and said pyridyl ring 9.1 optionally being substituted with 1-4 substituents, wherein said optional substituents for rings 9.0, 9.1, 10.0 and 11.0 are bound to the carbon atoms of said rings and are independently selected from the group consisting of: —NHC(O)R$^{15}$, —C(R$^{18}$)$_2$OR$^{19}$, —OR$^{15}$, —SR$^{15}$, F, Cl, Br, alkyl, substituted alkyl (as defined above in (b)), aryl, arylalkyl, cycloalkyl, or —N(R$^{15}$)$_2$; R$^{15}$ is as defined above; each R$^{18}$ is independently selected from the group consisting of: H and alkyl; R$^{19}$ is selected from the group consisting of: H and —C(O)NHR$^{20}$, and R$^{20}$ is as defined below;

R$^{13}$ and R$^{14}$ for each n are independently selected from the group consisting of: H, F, alkyl, aryl, arylalkyl, heteroaryl, heteroarylalkyl, cycloalkyl, cycloalkylalkyl, —CON(R$^{15}$)$_2$ (wherein R$^{15}$ is as defined above), —OR$^{15}$ and —N(R$^{15}$)$_2$ provided that the —OR$^{15}$ and —N(R$^{15}$)$_2$ groups are not bound to a carbon atom that is adjacent to a nitrogen atom, and provided that there can be only one —OH group on each carbon; and the substitutable R$^{13}$ and R$^{14}$ groups are optionally substituted with one or more substituents selected from the group consisting of: F, alkyl, cycloalkyl, arylalkyl, and heteroarylalkyl; or R$^{13}$ and R$^{14}$, for each n, together with the carbon atom to which they are bound, form a C$_3$ to C$_6$ cycloalkyl ring;

R$^9$ is selected from:

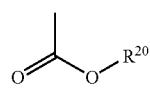
(12.0)

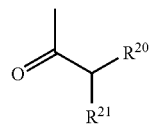
(13.0)

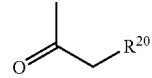
(14.0)

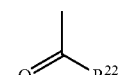
(15.0)

(16.0)

R$^{20}$ is selected from the group consisting of: H, alkyl, aryl, arylalkyl, cycloalkyl, cycloalkylalkyl, heteroaryl, heteroarylalkyl, heterocycloalkyl, and heterocyloalkylalkyl, provided that R$^{20}$ is not H when R$^9$ is group 12.0 or 16.0;

when R$^{20}$ is other than H, then said R$^{20}$ group is optionally substituted with one or more substituents selected from the group consisting of: halo, alkyl, aryl, —OC(O)R$^{15}$, —OR$^{15}$ and —N(R$^{15}$)$_2$, wherein each R$^{15}$ group is the same or different, and wherein R$^{15}$ is as defined above, provided that said optional substituent is not bound to a carbon atom that is adjacent to an oxygen or nitrogen atom;

R$^{21}$ is selected from the group consisting of: H, alkyl, aryl, arylalkyl, cycloalkyl, cycloalkylalkyl, heteroaryl, heteroarylalkyl, heterocycloalkyl and heterocycloalkylalkyl; and when R$^{21}$ is other than H, then said R$^{21}$ group is optionally substituted with one or more substituents selected from the group consisting of: alkyl and aryl; and R$^{22}$ is selected from the group consisting of: cycloalkyl, heterocycloalkyl, aryl, substituted aryl, alkyl, substituted alkyl and substituted cycloalkyl.

2. The compound of claim 1 selected from the group consisting of:

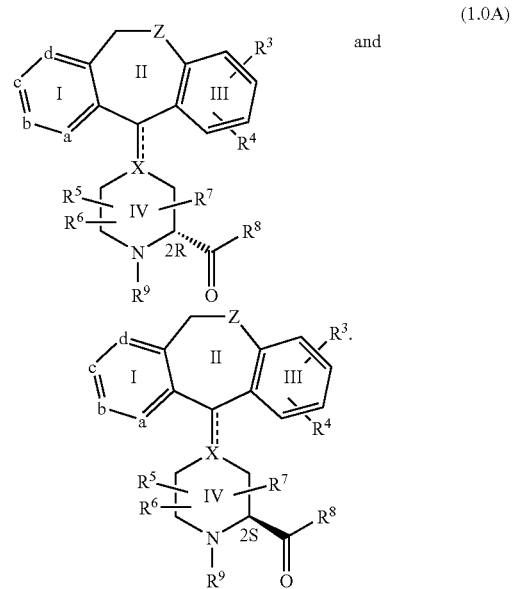
(1.0A)

3. The compound of claim 1 wherein $R^1$ to $R^4$ are independently selected from the group consisting of: H, Br, F and Cl; $R^5$ to $R^7$ are H; and a is N and the remaining b, c and d substituents are carbon.

4. The compound of claim 1 wherein $R^8$ is

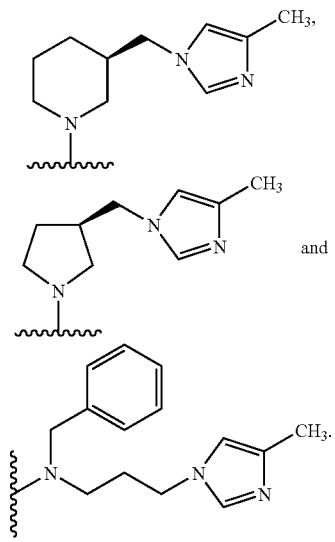

5. The compound of claim 1 wherein $R^{13}$ and $R^{14}$ are H.

6. The compound of claim 1 wherein Y is selected from the group consisting of: —S—, —S(O)—, —S(O$_2$)—, —O—, and —NR$^{16}$—.

7. The compound of claim 1 wherein $R^9$ is selected from the group consisting of groups 12.0, 13.0 and 15.0.

8. The compound of claim 1 wherein $R^1$ to $R^4$ are independently selected from the group consisting of: H, Br, F and Cl; $R^5$ to $R^7$ are H, a is N and the remaining b, c and d substituents are carbon; and Y is $CH_2$.

9. The compound of claim 8 wherein $R^{13}$ and $R^{14}$ are H.

10. The compound of claim 9 wherein $R^{12}$ is selected from the group consisting of: 9.0, 12.0, 13.0, and 15.0.

11. The compound of claim 9 wherein $R^{20}$ is selected from the group consisting of: t-butyl, i-propyl, neopentyl, cyclohexyl. and cyclopropylmethyl.

12. The compound of claim 9 wherein $R^9$ is selected from the group consisting of: 12.0 and 13.0, and $R^{21}$ for 13.0 is H.

13. A compound selected from the group consisting of:

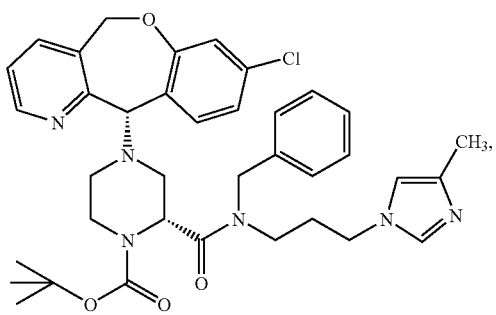
(1.1)

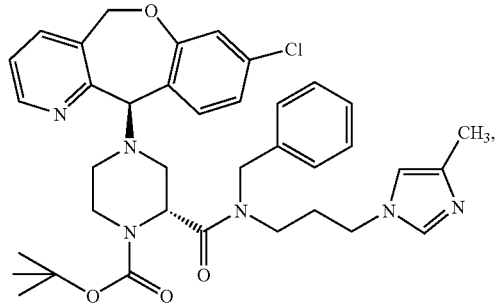
(1.2)

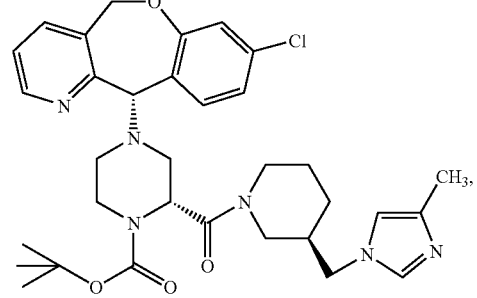
(1.3)

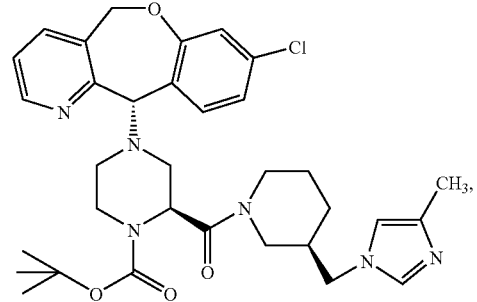
(1.4)

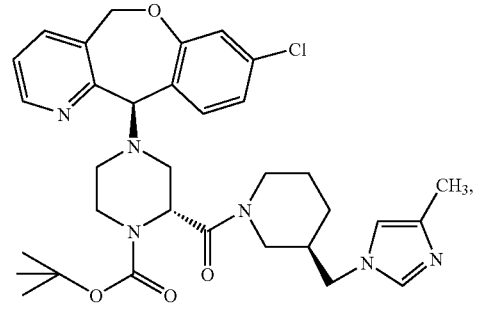
(1.5)

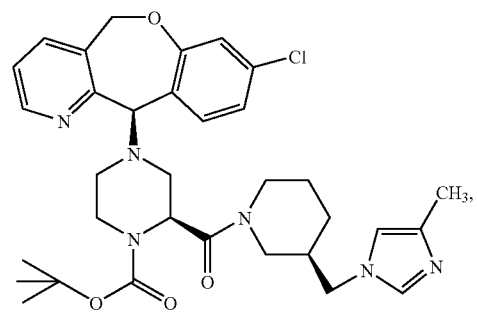
(1.6)

-continued
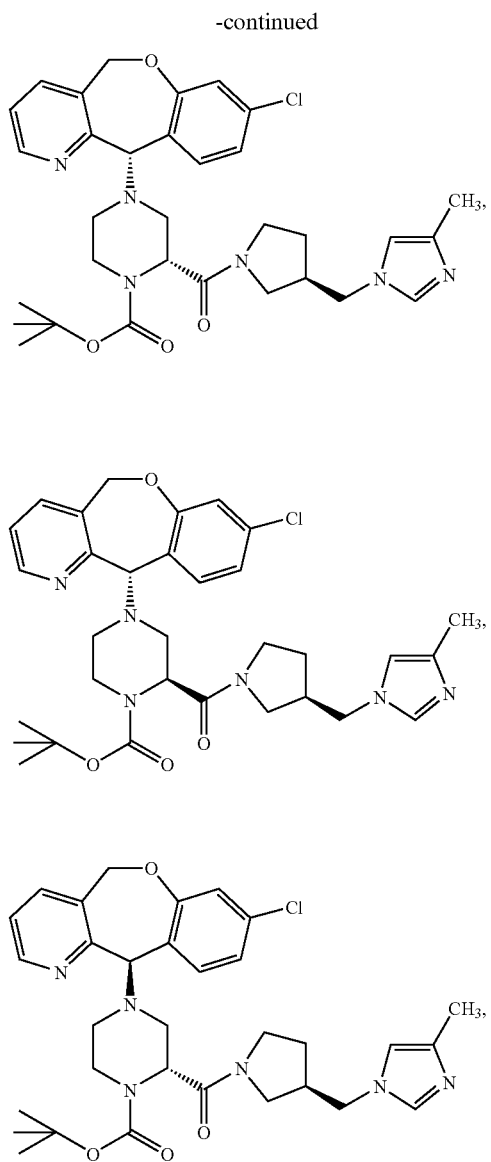
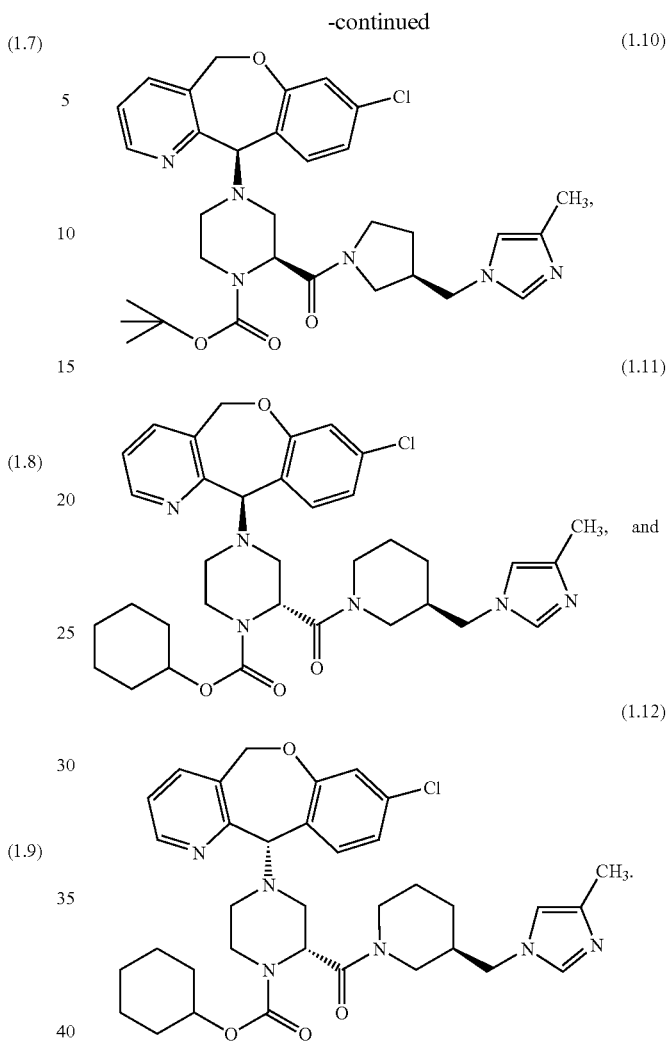
14. A pharmaceutical composition comprising an effective amount of at least one compound of claim 1 and a pharmaceutically acceptable carrier.
* * * * *